United States Patent [19]

Suzuki et al.

[11] Patent Number: 5,230,999
[45] Date of Patent: Jul. 27, 1993

[54] MONOCLONAL ANTIBODY TO ENDOTHELIN-3 OR PRECURSOR THEREOF AND USE THEREOF

[75] Inventors: Nobuhiro Suzuki; Hirokazu Matsumoto, both of Ibaraki, Japan

[73] Assignee: Takeda Chemical Industries, Ltd., Osaka, Japan

[21] Appl. No.: 555,081

[22] Filed: Jul. 18, 1990

[30] Foreign Application Priority Data

Jul. 24, 1989 [JP] Japan .................................. 1-188873
Jun. 18, 1990 [JP] Japan .................................. 2-157698

[51] Int. Cl.$^5$ ................... G01N 33/53; G01N 33/543; C12N 5/12; C07K 15/28
[52] U.S. Cl. ........................................ 435/71; 435/7.2; 435/240.27; 530/388.1; 530/388.24; 436/518
[58] Field of Search .................... 530/387, 388, 388.24, 530/388.1; 435/7.1, 7.2, 240.27; 436/518

[56] References Cited

FOREIGN PATENT DOCUMENTS 0331100 6/1989 European Pat. Off. .
2-27983 of 0000 Japan .

OTHER PUBLICATIONS

Matsumoto, H. et al, Biochem Biophys Res Com, 164 (1):74–80, Oct. 16, 1989.
Saito, et al., Biochem Biophys Res Com, 161(1):320–326, May 30, 1989.
Yanagisawa, M. et al., Proc. Natl. Acad. Sci, 85: 6964–6967, Sep. 1988.
Inoue, A. et al., Proc. Natl. Acad. Sci, 86: 2863–2867, Apr. 1989.
Nakajima, K. et al., J. of Card. Pharm., 13 (Suppl. 5): 58–512, 1989.
N. Suzuki, et al., Journal of Immunological Methods, 118, 245–250 (1989).
U.S. Ser. No. 07/317,680, date Feb. 1, 1989, Suzuki, et al.
U.S. Ser. No. 07/583,879, date Aug. 30, 1990, Onda et al.

Primary Examiner—David L. Lacey
Assistant Examiner—Susan L. Futrovsky
Attorney, Agent, or Firm—David G. Conlin; Peter F. Corless; Ernest V. Linek

[57] ABSTRACT

Disclosed are monoclonal antibodies having an affinity for endothelin-3 or a precursor thereof; a hybridoma cell which produces the monoclonal antibody; and an immunoassay of endothelin-3 and big endothelin-3, a precursor of endothelin-3, by a sandwich method or a competitive method. The monoclonal antibodies can be used as strong antagonists for endothelin-3 in various endothelin-3-related diseases, and the immunoassays make it possible to determine endothelin-3 and big endothelin-3 with high sensitivity.

6 Claims, 7 Drawing Sheets

MONOCLONAL ANTIBODY TO ENDOTHELIN-3 OR PRECURSOR THEREOF AND USE THEREOF

BACKGROUND OF THE INVENTION

The present invention relates to a novel and useful antibody having a specific affinity for endothelin-3 and a precursor of endothelin-3, for example, big endothelin-3 and more particularly to an antibody useful for development of assays of endothelin-3 and a precursor of endothelin-3, for example, big endothelin-3 on the basis of antigen-antibody reactions or for diagnosis and treatment of diseases related to endothelin-3.

Endothelin-1 is a peptide which consists of 21 amino acid residues and was discovered in a culture supernatant of vascular endothelial cells, and has very strong vascular smooth muscle constrictor activity and vasopressor activity. From the analysis of cDNA of endothelin-1, it has also been deduced that big endothelin-1 (a precursor of endothelin-1) comprised of about 40 amino acid residues exists as an intermediate in the course of its biosynthesis. Until now, monoclonal antibodies to endothelin-1 and big endothelin-1 have been prepared and high sensitive enzyme immunoassays have been developed, whereby it has become possible to widely extend research toward the elucidation of the physiological role of endothelin-1 and the pathologic role thereof. The use of the monoclonal antibodies having neutralizing activity as specific antagonists has revealed that endothelin-1 is deeply related to ischemic diseases, and further detailed research has been advanced for the relation between the plasma endothelin-1 level and its pathologic role, using the above assays.

On the other hand, from the analysis of chromosomal DNA, the sequences of endothelin-1 and endothelin-2 have been newly discovered, and it has been revealed that the endothelins form a gene family. In particular, endothelin-3 differs from endothelin-1 and endothelin-2 in 6 residues (underlined) of 21 amino acid residues, as shown below, and it has been reported that endothelin-3 is considerably weaker in vascular smooth muscle constrictor and vasopressor activities than endothelin-1 and endothelin-2. Endothelin-1 (porcine or human, which was also referred to as endothelin-α):

Cys Ser Cys Ser Ser Leu Met Asp Lys Glu Cys Val
Tyr Phe Cys His Leu Asp Ile Ile Trp

Endothelin-2 (human):

Cys Ser Cys Ser Ser Trp Leu Asp Lys Glu Cys Val
Tyr Phe Cys His Leu Asp Ile Ile Trp

Endothelin-3 (rat or human, which was also referred as endothelin-γ):

Cys Thr Cys Phe Thr Tyr Lys Asp Lys Glu Cys Val
Tyr Tyr Cys His Leu Asp Ile Ile Trp

Further, the analysis of cDNA of endothelin-3 has revealed the structure of a precursor of endothelin-3 (Japanese Patent Unexamined Publication No. 1-253797/1989), and it has been suggested that endothelin-3 is synthesized from big endothelin-3 as a direct precursor, having the following sequence:

| Cys | Thr | Cys | Phe | Thr | Tyr | Lys | Asp | Lys | Glu | Cys | Val | Tyr | Tyr |
| Cys | His | Leu | Asp | Ile | Ile | Trp | Ile | Asn | Thr | Pro | Glu | Gln | Thr | Val |
| Pro | Tyr | Gly | Leu | Ser | Asn | Tyr | Arg | Gly | Ser | Phe | Arg | X |

(wherein X is Gly—OH, Gly—NH2, Gly—Lys—OH or Gly—Lys—Arg—OH.)

The structure of an additional precursor of endothelin-3 has been deduced, and is a polypeptide having the following amino acid sequence:

| Met | Glu | Pro | Gly | Leu | Trp | Leu | Leu | Phe | Gly | Leu | Thr | Val | Thr | Ser | Ala |
| Ala | Gly | Phe | Val | Pro | Cys | Ser | Gln | Ser | Gly | Asp | Ala | Gly | Arg | Arg | Gly |
| Val | Ser | Gln | Ala | Pro | Thr | Ala | Ala | Arg | Ser | Glu | Gly | Asp | Cys | Glu | Glu |
| Thr | Val | Ala | Gly | Pro | Gly | Glu | Glu | Thr | Val | Ala | Gly | Pro | Gly | Glu | Gly |
| Thr | Val | Ala | Pro | Thr | Ala | Leu | Gln | Gly | Pro | Ser | Pro | Gly | Ser | Pro | Gly |
| Gln | Glu | Gln | Ala | Ala | Glu | Gly | Ala | Pro | Glu | His | His | Arg | Ser | Arg | Arg |
| Cys | Thr | Cys | Phe | Thr | Tyr | Lys | Asp | Lys | Glu | Cys | Val | Tyr | Tyr | Cys | His |
| Leu | Asp | Ile | Ile | Trp | Ile | Asn | Thr | Pro | Glu | Gln | Thr | Val | Pro | Tyr | Gly |
| Leu | Ser | Asn | Tyr | Arg | Gly | Ser | Phe | Arg | Gly | Lys | Arg | Ser | Ala | Gly | Pro |
| Leu | Pro | Gly | Asn | Leu | Gln | Leu | Ser | His | Arg | Pro | His | Leu | Arg | Cys | Ala |
| Cys | Val | Gly | Arg | Tyr | Asp | Lys | Ala | Cys | Leu | His | Phe | Cys | Thr | Gln | Thr |
| Leu | Asp | Val | Ser | Arg | Gln | Val | Glu | Val | Lys | Asp | Gln | Gln | Ser | Lys | Gln |
| Ala | Leu | Asp | Leu | His | His | Pro | Lys | Leu | Met | Pro | Gly | Ser | Gly | Leu | Ala |
| Leu | Ala | Pro | Ser | Thr | Cys | Pro | Arg | Cys | Leu | Phe | Gln | Glu | Gly | Ala | Pro |

Thus, the results of the studies of their structure and pharmacological activity strongly suggest that endothelin-3 forms a receptor system different from those of endothelin-1 and endothelin-2, and a deep interest is taken in the physiological role of endothelin-3.

Although the interest in the physiological role of endothelin-3 is increased as described above, basic physiological information such as the expression site or plasma level of endothelin-3 has scarcely been obtained until now. This is mainly caused by that any monoclonal antibodies specifically recognizing endothelin-3 or the precursor of endothelin-3 have hitherto not been prepared and that any immunoassays for specifically, high sensitively assaying endothelin-3 or the precursor of endothelin-3 have not been developed. These immunological procedures are considered to be one of the most effective means to study endothelin-3, particularly its metabolic pathways, secretory mechanism, receptor system, relation to the pathology and the like as a whole. The establishment of these procedures has therefore been earnestly desired in various fields.

SUMMARY OF THE INVENTION

The present inventors have prepared a monoclonal antibody having binding specificity for endothelin-3 or a precursor of endothelin-3, for example, big endothelin-3 and developed an immunoassay by which endothelin-3 or big endothelin-3 is specifically, high sensitively detectable using the antibody. Further, the present inventors have discovered a pharmacological activity characteristic of the antibody, namely that the antibody depressed the endothelin-3-inducing constriction of smooth muscles of various animals. This information shows that the antibody can be used as a specific antagonist to endothelin-3, and therefore indicates that the antibody can be used as preventive or therapeutic drugs for various diseases causally or symptomatically related to endothelin-3.

In accordance with the present invention, there are provided a monoclonal antibody having an affinity for endothelin-3 or a precursor of endothelin-3; a hybridoma which produces the above monoclonal antibody; and an immunoassay of endothelin-3 and a ,precursor of endothelin-3, for example, big endothelin-3 by a sandwich method or a competitive method.

BRIEF DESCRIPTION OF THE DRAWINGS

FIG. 1 is a graph showing standard curves of endothelin-3 and endothelin-1 obtained by the competitive method-enzyme immunoassay using monoclonal antibody AET-30a;

FIG. 3 (A) is a graph showing standard curves of big endothelin-3 (-▲-), big endothelin-1 (human) (-○-), endothelin-3 (-●-), big endothelin-3 C-terminal peptide(2-2-42) (-■-) and big endothelin-3 C-terminal peptide(2-2-41)-$NH_2$ (-□-) obtained by the competitive method-enzyme immunoassay using monoclonal antibody bET-31a;

FIG. 3 (B) is a graph showing standard curves of big endothelin-3 (-▲-), big endothelin-1 (human) (-○-), endothelin-3 (-●-), big endothelin-3 C-terminal peptide(2-2-42) (-■-) and big endothelin-3 C-terminal peptide(2-2-41)-$NH_2$ (-□-) obtained by the competitive method-enzyme immunoassay using monoclonal antibody bET-23a;

FIG. 4 is a graph showing standard curves of big endothelin-3 (-▲-), big endothelin-1 (human) (-○-), endoethelin-3 (-●-), endothelin-1 (-■-) and endothelin-2 (-□-) obtained by the sandwich method-enzyme immunoassay using monoclonal antibody AET-30a and monoclonal antibody bET-31a;

FIG. 5 is a graph showing standard curves of big endothelin-3 (-▲-), big endothelin-1 (human) (-○-), endoethelin-3 (-●-), endothelin-1 (-■-) and endothelin-2 (-□-) obtained by the sandwich method-enzyme immunoassay using monoclonal antibody AET-30a and monoclonal antibody bET-23a;

Figure 7:
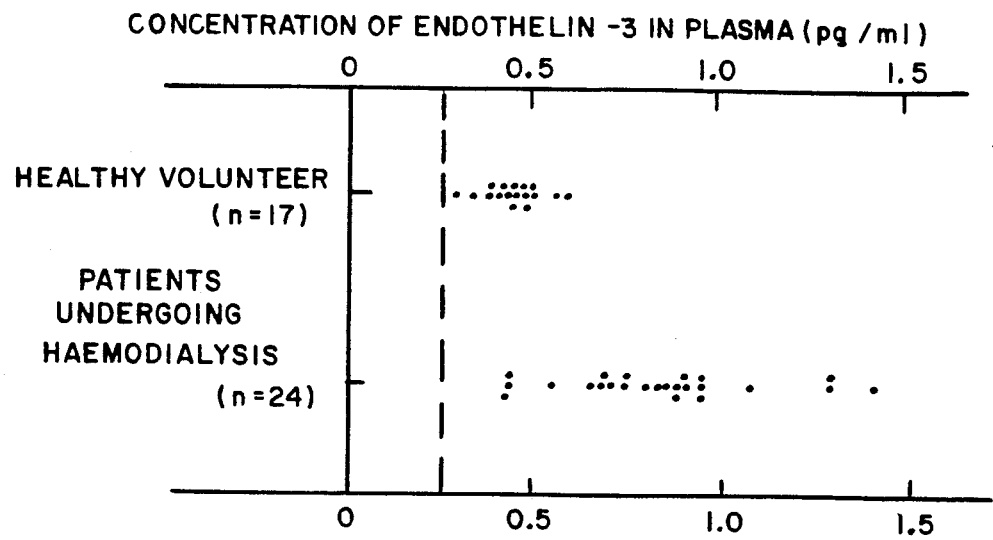

ET-3: Endothelin-3; a: Oxide of human big endothelin-1; hbig-ET-1:Human big endothelin-1; b: Oxide of endothelin-1; pbig-ET-1: Porcine big endothelin-1; ET-1: Endothelin-1; and ET-2: Endothelin-2;

FIG. 7 is a graph showing the concentrations of endothelin-3 in plasma of healthy volunteers and patients undergoing haemodialysis; and FIG. 8A is a graph showing the results detected by separation of endothelin-3 immunoactivity in plasma of healthy volunteers and patients undergoing haemodialysis by reverse-phase HPLC, and B by the above sandwich method-enzyme immunoassay.

DESCRIPTION OF THE PREFERRED EMBODIMENTS

In the sandwich methods of endothelin-3, antibodies used for the first reaction and the second reaction, respectively, may be polyclonal antibodies or monoclonal antibodies. However, it is preferred that one is an anti-endothelin-3 monoclonal antibody which reacts with endothelin-3, but does not react with a C-terminal portion of endothelin-3, and the other is an anti-endothelin-3 polyclonal or monoclonal antibody which reacts with the C-terminal portion of endothelin-3. The latter anti-endothelin-3 polyclonal or monoclonal antibodies which react with the C-terminal portion of endothelin-3 include the same antibody as that which reacts with the C-terminal portion of endothelin-1 or endothelin-2, as known from the above comparison of the amino acid sequence of endothelin-3 with those of endothelin-1 and endothelin-2. This is mentioned in Japanese Patent Unexamined Publication No. 1-46560/1989.

Also in the sandwich methods of big endothelin-3, it is preferred that one of antibodies used for the first reaction and the second reaction is a monoclonal antibody which reacts with big endothelin-3, but does not react with endothelin-3, and the other is a monoclonal antibody which reacts with endothelin-3. With respect to the monoclonal antibodies which react with big endothelin-3, but do not react with endothelin-3, there are particularly preferably used antibodies having broad specificity for the structure of a C-terminal portion of big endothelin-3, for example, antibodies which react to a similar degree, whether the C-terminal portion of the sequence is Arg—Gly or Arg—$NH_2$.

The polyclonal antibody of the present invention is usually prepared by producing a conjugate of a carrier protein with endothelin-3, big endothelin-3 or a partial peptide thereof, which acts as an immunogen; inoculating animals with this conjugate; collecting a substance containing a desired antibody from the immunized animals; and performing separation and purification of the antibody.

The monoclonal antibody of the present invention is prepared by selecting individuals having a high antibody titer from the above immunized animals; collecting spleens or lymphatic corpuscles therefrom 2 to 5 days after the final immunization; fusing antibody producing cells contained therein with myeloma cells; and selecting hybridoma cells which stably produces an antibody having a high titer to obtain monoclonal hybridoma cells.

As immunogens, there can be used, for example, both of natural purified samples and synthetic samples. The above-mentioned endothelin-3, big endothelin-3 and partial peptide thereof are used. In some cases, compound containing the structure of endothelin-3 or a portion thereof may be used as immunogens.

Various peptides used in the present invention can be prepared by methods known to those skilled in the art for synthesizing peptides, for example, any of the solid phase synthesis methods and the liquid phase synthesis methods may be used. For example, when endothelin-3 is synthesized by the solid phase methods, it is preferable to use the solid phase peptide synthesis method of Merryfield (*J. Am. Chem. Soc.* 85, 2149 (1963). There may be used any of the insoluble resins known in the art. Examples of such resins include polystyrene-type resins such as chloromethylated styrene-divinylbenzene copolymers and phenacylacetic methylated styrene-divinylbenzene copolymers, and polyamide-type resins such as polydimethylacrylamide resins. After a C-terminal N-protected amino acid has been bound to the insoluble resin, protected amino acids are successively combined from the side of the C-terminus of endothelin-3 according to known methods. Then, the resultant product is treated with hydrogen fluoride, followed by formation of disulfide bonds, whereby the desired endothelin-3 can be synthesized. As the N-protected amino acids, all of α-amino acid groups are preferably protected with the Boc group. It is preferred that the hydroxyl group of serine and threonine is protected with the Bzl group, the ω-carboxylic acids of glutamic acid and aspartic acid is protected with the OBzl group, the ε-amino group of lysine is protected with the Cl-Z group, the thiol group of cysteine is protected with the Acm group or the MeBzl group, the hydroxyl group of tyrosine is protected with the Br-Z group, the imidazole group of histidine and the guanido group of arginine are protected with the Tos group, and the indole group of tryptophan is protected with the CHO group.

Procedures for synthesis in accordance with the liquid phase methods include the methods described in Schröder and Lubke, *The Peptides*, vol. 1, Academic Press, New York, U.S.A. (1966) or Izumiya et al., *Peptide Synthesis*, Maruzen (1975), such as the azido method, the chloride method, the acid anhydride method, the mixture anhydride method, the DCC method, the active ester method, the method using Woodward reagent K, the carbodiimidazole method, the redox method and the DCC/additive (for example, HONB, HOBt or HOSu) method.

For the protein conjugates of immunogens and the carrier proteins used for immunizing mammals, any type of carrier protein may be used and the carrier may be added to a hapten at any ratio, as long as the antibody can be effectively produced to the hapten coupled with the carrier and immunized. For example, bovine serum albumin, bovine thyroglobulin or hemocyanin is coupled with the hapten at a weight ratio of 0.1 to 20, preferably 1 to 5, per 1 of the hapten.

Various condensing agents may be used for the coupling of the haptens and the carriers. In particular, glutaraldehyde, carbodiimide and maleimide active esters are preferably used.

The condensed products are administered to warm-blooded animals at sites where the antibody is capable for being produced, alone or with carriers or with diluents. Particularly, the subcutaneous injection is preferred. In order to enhance the antibody productivity upon the administration, Freund's complete adjuvant or Freund's incomplete adjuvant may be administered. The administration is usually carried out 1 time every 2 to 6 weeks.

The warm-blooded animals used therein include, for example, monkey, rabbit, dog, guinea pig, mouse, rat, sheep, goat and chicken.

The antibodies are harvested from the blood, the ascites and the like (preferably the blood) of the warm-blooded animals immunized by the methods described above. When the immunogen is, for example, endothelin-3 or a partial peptide thereof, the titer of the anti-endothelin antibody in the antiserum is assayed by, for example, reacting labeled endothelin-3 described below with the antiserum, and then measuring the activity of a labeling agent combined with the antibody. The antibodies are isolated and purified in accordance with methods known in the art for isolating and purifying immunoglobulin. Such methods include salt precipitation, alcohol precipitation, isoelectric precipitation, electrophoresis, adsorption and description using an ion exchanger (for example, DEAE), ultracentrifugation, gel-permeation chromatography, and affinity chromatography.

The antibodies thus obtained comprise mainly of IgG and contain also additional immunoglobulins such as IgM and IgA.

On the other hand, the anti-endothelin-3 antibody producing hybridoma can be prepared by selecting individuals having a high antibody titer from the warm-blooded animals such as mice immunized similarly to the above method for preparing the polyclonal antibody, collecting spleens or lymphatic corpuscles therefrom 2 to 5 days after the final immunization, and fusing antibody producing cells contained therein with myeloma cells. The fusing operation may be conducted according to known methods, for example, the method of Kohler and Milstein [*Nature*, 256, 495 (1975)]. Fusion accelerators include polyethylene glycol (PEG) and Sendai virus. In particular, PEG is preferably used. The myeloma cells include, for example, NS-1, P3U1 and SP2/0. In particular, P3U1 is preferably used. The ratio of the number of the antibody producing cells (lien cells) to the number of the myeloma cells is preferably about 1:1 to 20:1. PEG (preferably PEG 1,000 to PEG 6,000) is added in a concentration of about 10 to 80%, and incubated at 20° to 40° C., preferably 30° to 37° C., for 1 to 10 minutes, whereby the cell fusion is effectively performed.

The anti-endothelin-3 antibody producing hybridoma cells or the anti-big endothelin-3 antibody producing hybridoma cells can be screened by various methods known in the art. Examples of such methods include an enzyme-linked immunosorbent assay (ELISA) which comprises adding hybridoma culture supernatant to a solid phase (for example, a microtiter plate) allowed to adsorb endothelin-3, big endothelin-3 or the partial peptide thereof, then adding the anti-immunoglobulin antibody (when mouse cells are used for the cell fusion, the anti-mouse immunoglobulin antibody is used) labeled with horseradish peroxidase (HRP) or protein A thereto, and detecting the labeled monoclonal antibody bound to the solid phase; and an enzyme immunoassay which comprises adding hybridoma culture supernatant to a solid phase allowed to adsorb the anti-immunoglobulin antibody or protein A, then adding endothelin-3, big endothelin-3 or the partial peptide thereof labeled with HRP, and detecting the monoclonal antibody bound to the solid phase. Selection and breeding of hybridoma cells are usually achieved by addition of HAT (hypoxanthine, aminopterin and thymidine) and by use of a medium for animal cells containing 10 to 20% fetal calf serum, such as RPMI 1640. The antibody titer of the hybridoma culture supernatant can be measured similarly to the above method for measuring the titer of the anti-endothelin antibody in antiserum.

Isolation and purification of the anti-endothelin-3 monoclonal antibody or the anti-big endothelin-3 antibody are conducted in accordance with the method for isolating and purifying immunoglobulin, similarly to the separation and purification of the polyclonal antibody described above.

The anti-endothelin-3 polyclonal antibody reactive to a partial region of endothelin-3 can be prepared by the above-mentioned method using a peptide corresponding to this partial region as a hapten for immunization. Further, the anti-endothelin-3 polyclonal antibody can also be prepared from the anti-endothelin-3 polyclonal antibody prepared by using endothelin-3 as a hapten, by use of affinity chromatography employing a column combined with a peptide corresponding to the above partial region.

The anti-big endothelin-3 polyclonal antibody reactive to a partial region of big endothelin-3 can be prepared by the above-mentioned method using a peptide corresponding to this partial region as a hapten for immunization. Further, such anti-big endothelin-3 monoclonal antibody can also be prepared from the anti-big endothelin-3 polyclonal antibody prepared by using big endothelin-3 as a hapten, by use of affinity chromatography employing a column combined with a peptide corresponding to the above partial region.

Screening for hybridoma cells producing the monoclonal antibody reactive to endothelin-3 or the partial region of big endothelin-3 and hybridoma cells producing the monoclonal antibody reactive to endothelin-3 or big endothelin-3 but not reactive to the partial region thereof can be accomplished, for example, by assaying an affinity of the peptide corresponding to the above partial region for the antibody produced by the hybridoma cells.

In particular, for screening of a monoclonal antibody recognizing a site other than endothelin-3 C-terminal peptide Cys His Leu Asp Ile Ile Trp, it is preferable to employ a sandwich-type EIA using a marker for an antibody to the above C-terminal peptide. Namely, such an EIA comprises adding hybridoma culture supernatant to a solid phase allowed to adsorb the anti-immunoglobulin antibody or protein A, further adding endothelin-3 thereto, and then reacting the anti-endothelin-3 C-terminal peptide antibody labeled with HRP therewith, followed by assay of enzyme activity on the solid phase.

By using the anti-endothelin-3 or anti-big endothelin-3 monoclonal antibody obtained above, assay and tissue staining of endothelin-3 can be carried out. Endothelin-3 and big endothelin-3 are usually assayed by competitive methods which will be described below. However, it is preferable to use sandwich methods which will be described below.

In the competitive methods, the anti-endothelin-3 or anti-big endothelin-3 antibody obtained by the present invention is competitively reacted with a test solution and endothelin-3 or big endothelin-3 or the partial peptide thereof which is labeled with a labeling agent, followed by measurement of the ratio of the labeling agent bound to the antibody to determine the amount of endothelin-3, big endothelin-3 or the partial peptide thereof contained in the test solution.

The labeling agents for endothelin-3, big endothelin-3 or the partial peptide thereof, or the labeling agents for the antibody described later include radioisotopes, enzymes, fluorescent substances and luminous substances. The radioisotopes include, for example, $^{125}I$, $^{131}I$, $^{3}H$ and $^{14}C$. The enzymes which are stable and high in specific activity are preferably used. Examples of such enzymes include $\beta$-galactosidase, $\beta$-glucosidase, alkaline phosphatase, peroxidase and malate dehydrogenase. The fluorescent substances include fluorescamine and fluorescein isothiocyanate. The luminous substances include luminol, luminol derivatives, luciferin and lucigenin. Further, a biotin-avidin system may also be used in order to bind the labeling agents to the antibody, or to endothelin-3, big endothelin-3 or the partial peptide of big endothelin-3.

For example, when the activity of the labeling agents described above is measured for endothelin-3, it is necessary to separate labeled endothelin bound to the antibody from free labeled endothelin. This separation is hereinafter referred to as B/F separation for brevity. When the enzyme is used as the labeling agent, there is advantageously used an active adsorbent such as an insolubilized antibody to the anti-endothelin-3 antibody or insolubilized protein A, as a reagent for the B/F separation. For example, an anti-IgG antibody (corresponding to the antibody to the anti-endothelin-3 antibody) is used as the solid phase, and labeled endothelin-3 is bound to the anti-IgG antibody of the solid phase through the above antibody reactive thereto to measure the labeling agent on the solid phase.

When the enzyme is used as the labeling agent, the activity of the enzyme on an insolubilized carrier is usually determined by colorimetric methods or fluorescent methods.

When the non-protein substance such as the radioisotope is used as the labeling agent, there are used for the B/F separation reagents other than the reagents described above, such as an antibody to the anti-endothelin-3 which is not insolubilized, sodium sulfate, dextran charcoal powder and polyethylene glycol. In any methods, the activity of the labeling agent in the supernatant or in the precipitate is assayed.

The above insolubilization may be achieved by physical adsorption or chemical bonding usually used for insolubilizing or immobilizing proteins or enzymes. The carriers include polysaccharides such as agarose, dextran and cellulose; synthetic resins such as polystyrene, polyacrylamide and silicone; and glass.

In the competitive methods, for example, in the case of assay of endothelin-3, there may be reacted in any order the anti-endothelin-3 antibody, the test solution, labeled endothelin-3 and the reagent for the B/F separation. Also, all or a part of them may be reacted at the same time. It is however preferable that at least labeled endothelin-3 is added to the reaction system simultaneously with the reaction of the test solution and the anti-endothelin-3 antibody, or after the reaction was completed.

The reagent for the B/F separation such as sodium sulfate, dextran charcoal powder or polyethylene glycol is mainly added to the reaction system at the final stage thereof.

On the other hand, in the sandwich methods, the test solution is brought into contact with (or reacted with) the insolubilized anti-endothelin-3 or big endothelin-3 antibody (the first reaction), and further the labeled anti-endothelin-3 or big endothelin-3 antibody is reacted therewith (the second reaction), followed by assay of the activity of the labeling agent on the insolubilized carrier to determine the amount of endothelin-3 or big endothelin-3 in the test solution. The first and second reactions may be conducted at the same time or at different times. The labeling agents and the insolubilizing methods can conform to those described above.

As the anti-endothelin-3 or big endothelin-3 antibody used in the second reaction, there is preferably used the antibody different from the anti-endothelin-3 or big endothelin-3 antibody used in the first reaction in the site to which endothelin-3 or big endothelin-3 is bound. For example, in the case of the assay of endothelin-3, if the activity used in the first reaction has the binding capacity to the C-terminal portion of endothelin-3, in the second reaction is preferably used the anti-endothelin-3 antibody which can be bound to a site other than the C-terminal portion, for example, to the N-terminal portion. On the other hand, if the antibody used in the first reaction has the binding activity to the N-terminal portion of endothelin-3, in the second reaction is preferably used the anti-endothelin-3 antibody which can be bound to a site other than the N-terminal portion,,for example, to the C-terminal portion.

Each of the antibodies used in the first and second reactions may be a polyclonal antibody or a monoclonal antibody. However, for example, in the case of the assay of endothelin-3, it is preferable that one is an anti-endothelin-3 monoclonal antibody which reacts with endothelin-3, but does not react with the C-terminal portion of endothelin-3, and the other is an anti-endothelin-3 polyclonal or monoclonal antibody which reacts with the C-terminal portion of endothelin-3.

In the immunoassays of endothelin-3 by the sandwich methods, there are preferably used an anti-endothelin-3 polyclonal antibody which reacts with the C-terminal peptide of endothelin-3, namely Cys-His-Leu-Asp-Ile-Ile-Trp, and an endothelin-3 monoclonal antibody which reacts with endothelin-3, but does not react with the above C-terminal peptide of endothelin-3.

In the immunoassays by the sandwich methods, both of the antibody for solid phase and the antibody for labeling may be antibodies of any class and subclass, and may be F(ab')$_2$, Fab' or Fab fractions which are obtained by removing Fc' or Fc fractions therefrom, as long as they have antibody activity.

In the immunoassays by the sandwich methods, when the monoclonal antibody is used, it is not always necessary to use one kind of antibody as the antibody for solid phase or the antibody for labeling. For the purpose of improving assaying sensitivity, mixtures of two or more kinds of antibodies can be used.

Further, the immunoassays using the antibodies which are obtained according to the present invention can be used for diagnosis and treatment of diseases in which endothelin-3 participates.

As test samples, there can be used humors such as plasma, serum, urine, cerebrospinal fluid, ascites, pleural fluid and amniotic fluid, sputum and feces. These samples can be used for the immunoassays as such or with concentration after dilution or extraction with various buffers. Any buffers or organic solvents can be used as solvents for dilution or extraction of the samples. Preferred examples thereof include buffers for immunoassay, water, saline, acetate buffer, acetone, chloroform-methanol and these solutions containing surface active agents. The samples can be directly concentrated under reduced pressure or under ordinary pressure in a stream of nitrogen. Also, the samples can be added to carriers for ion exchange or reverse-phase chromatography, or to carriers to which the anti-endothelin-3 is bonded, and then eluted under appropriate conditions, followed by concentration under reduced pressure or under ordinary pressure in a stream of nitrogen. It is particularly preferable to use cartridge C2, C8 or C18, a carrier for reverse-phase chromatography, as the carrier for concentration. The condensates are dissolved in buffers for immunoassay,, and then subjected to the immunoassays.

Further, the anti-endothelin-3 and big endothelin-3 antibodies obtained in the present invention can also be used for immunohistochemical stain of endothelin-3 and big endothelin-3. The methods thereof include, for example, the direct method using the labeled anti-endothelin-3 or anti-big endothelin-3 antibody, and the indirect method using the anti-endothelin-3 or anti-big endothelin-3 antibody and the labeled antibody to the anti-endothelin-3 or anti-big endothelin-3 antibody.

Furthermore, of the anti-endothelin-3 antibodies obtained by the present invention, the antibody which is able to neutralize the vasoconstrictor activity of endothelin-3 can be employed as a specific antagonist to endothelin-3.

As methods for screening an antibody specifically depressing the activity of endothelin-3 from the anti-endothelin- 3 antibodies, any methods for detecting the pharmacological activity of endothelin-3 can be used. Examples of such methods include an in vitro assay system in which various vascular smooth muscle constrictor activities of pig, rat, rabbit, guinea pig, dog and human are used as an indication, and an in vivo assay system in which the vasopressor or vasodepressor activity of the above animals is used as an indication.

The antibodies specifically depressing the activity of endothelin-3 may be antibodies of ,any class, such as IgG, IgA and IgM, and may be Fab' or Fab fractions which are obtained by removing Fc' or Fc regions therefrom, or polymers of the fractions. There can also be used a chimera antibody obtained by fusing a variable gene region of a monoclonal antibody which can specifically depress the activity of endothelin-3 with a constant gene region of human immunoglobulin, followed by expression as a recombinant.

When bases, amino acids and so on are indicated by the abbreviations in this specification and drawings, the abbreviations adopted by IUPAC-IUB Commission on Biochemical Nomenclature or commonly used in the art are employed. For example, the following abbreviations are used. When the optical isomers are capable of existing with respect to the amino acid, the L-form is represented unless otherwise specified.

DNA: Deoxyribonucleic acid
A: Adenine
C: Cytosine
G: Guanine
T: Thymine
Ala: Alanine
Arg: Arginine
Asn: Asparagine
Asp: Aspartic acid
Cys: Cysteine
Gln: Glutamine
Glu: Glutamic acid
Gly: Glycine
His: Histidine
Ile: Isoleucine
Leu: Leucine
Lys: Lysine
Met: Methionine
Phe: Phenylalanine
Pro: Proline
Ser: Serine
Thr: Threonine Trp: Tryptophan
Tyr: Tyrosine
Val: Valine
Boc: t-Butyloxycarbonyl
MeBzl: p-Methylbenzyl
Bzl: Benzyl
P: Polystyrene resin for solid synthesis of peptide
PAM: p-Oxymethylphenylacetamidomethyl resin
AcOH: Acetic acid
OBzl: Benzyl ester
Tos: Tosyl
Br-z: 2-Bromobenzyloxycarbonyl
Cl-z: 2-Chlorobenzyloxycarbonyl The present invention will hereinafter be described in detail with the following Examples, It is understood of course that these Examples are not intended to limit the scope of the invention.

Hybridoma AET-30 which is used in the Examples described below and which produces mouse monoclonal antibody AET-30a is deposited with the Institute for Fermentation, Osaka, Japan (IFO) under the accession number IFO 50193 on July 7, 1989. This hybridoma is also deposited with the Fermentation Research Institute, Agency of Industrial Science and Technology, Ministry of International Trade and Industry, 1-3, Higashi 1-chome, Tsukuba-shi, Ibaraki-ken 305 Japan (FRI) under the accession number FERM BP-2523 in accordance with the Budapest Treaty on Jul. 20, 1989.

Hybridoma bET-31 which is used in the Examples described below and which produces mouse monoclonal antibody bET-31a is deposited with the Institute for Fermentation, Osaka, Japan (IFO) under the accession number IFO 50247 on May 24, 1990. This hybridoma is also deposited with the Fermentation Research Institute, Agency of Industrial Science and Technology, Ministry of International Trade and Industry, 1-3, Higashi, 1-chome, Tsukuba-shi, Ibraki-ken 305 Japan (FRI) under the accession number FERM BP-2949 in with the Budapest Treaty on Jun. 12, 1990.

Hybridoma bET-23 which is used in the Examples described below and which produces mouse monoclonal antibody bET-23a is deposited with the Institute for Fermentation, Osaka, Japan (IFO) under the accession number IFO 50246 on May 24, 1990. This hybridoma is also deposited with the Fermentation Research Institute, Agency of Industrial Science and Technology, Ministry of International Trade and Industry, 1-3, Higashi 1-chome, Tsukuba-shi, Ibaraki-ken 305 Japan (FRI) under the accession number FERM BP-2948 in accordance with the Bundapest Treaty on Jun. 12, 1990.

EXAMPLE 1

Preparation of Enzyme-Labeled Anti-Endothelin-3 C-Terminal Peptide Antibody

1. Synthesis of Peptide (A) Synthesis of H-Cys-His-Leu-Asp-Ile-Ile-Trp-OH (C-Terminal Portion of Endothelin-3)

Boc-Ile-Trp- OBzl: In 100 ml of DMF was dissolved 84 g of H-Trp-OBzl-pTsOH, and neutralized with 25 ml of triethylamine (TEA). Thereafter, Boc-Ile-ONB prepared from 48.9 g of Boc-Ile-OH·½H$_2$O, 40.12 g of N-hydroxy-5-norbornene-2,3-dicarboxiimide (HONB) and 46.20 g of dicyclohexylcarbodiimide (DCC) was added thereto and stirred overnight. The solvent was removed therefrom by distillation under reduced pressure. The residue thus formed was dissolved by adding 400 ml of diethyl ether and 20 ml of ethyl acetate. The resulting solution was washed with 0.5 N HCl and 5% aqueous NaHCO$_3$, and then with water. Thereafter, the solution was dried with anhydrous MgSO$_4$. After the solvent was distilled off, petroleum ether was added to the residue and crystals were obtained by filtration. The yield was 83.1 g (90.9%).

$[\alpha]_D^{18}$ −19.7° (c=0.99 MeOH).

Elemental analysis: As C$_{29}$H$_{37}$N$_3$O$_5$ Calculated: C, 68.62; H, 7.35; N, 8.28. Found: C, 68.69; H, 7.35; N, 8.16.

Boc-Ile-Ile-Trp-OBzl: In 120 ml of dioxane was dissolved 53.3 g of Boc-Ile-Trp-OBzl, and 160 ml of 7.1 N HCl- dioxane was added thereto under ice cooling, followed by stirring for 90 minutes. After the solvent was removed therefrom by distillation under reduced pressure, diethyl ether was added to the residue and then the precipitate was filtered. This precipitate was dissolved in a mixed solvent of 150 ml of acetonitrile and 250 ml of DMF and neutralized with 14.6 ml of TEA under ice cooling. Then, precipitated TEA.HCl was filtered off. To the filtrate, 45.33 g of Boc-Ile-ONB was added, and stirred overnight. After the solvent was removed by distillation, the residue was dissolved in 1 liter of CHCl$_3$, washed with 0.5 N HCl, 5% NaHCO$_3$, and dried with anhydrous MgSO$_4$. After the solvent was distilled off under reduced pressure, diethyl ether was added to the residue and the precipitate was filtered as crystals. Then, the precipitate was washed with acetonitrile and diethyl ether, and dried. The yield was 54.95 g (84.3%).

$[\alpha]_D^{18}$ −12.0° (c=0.98 CHCl$_3$).

Elemental analysis: As C$_{35}$H$_{48}$N$_4$O$_6$ Calculated: C, 67.72; H, 7.79; N, 9.03. Found: C, 67.72; H, 7.91; N, 8.87.

Boc-Asp-(OBzl)-Ile-Ile-Trp-OBzl: In 250 ml of trifluoroacetic acid (TFA) containing 10% 1,2-ethanedithiol was dissolved 49.7 g of Boc-Ile-Ile-Trp-OBzl under ice cooling, and the resulting solution was allowed to stand at room temperature for 15 minutes. The solvent was removed therefrom by distillation and 20 ml of 4 N HCl-dioxane was added to the residue, followed by stirring. Then, diethyl ether was added thereto and the precipitate was filtered. This precipitate was dissolved in 250 ml of DMF and neutralized with 11.1 ml of TEA under ice cooling. Then, precipitated TEA.HCl was filtered off. To the filtrate was added Boc-Asp-(OBzl)-QNB prepared from 31.0 g of Boc-Asp-(OBzl)-OH, 20.6 g of HONB and 23.8 of DCC, and the resulting solution was stirred overnight. After the solvent was removed by distillation under reduced pressure, 800 ml of ethyl acetate was added to the residue to dissolve it. The resulting solution was washed with 10% aqueous citric acid, 5% NaHCO$_3$ and water, and dried with anhydrous MgSO$_4$. After the solvent was distilled off under reduced pressure, diethyl ether was added to the residue and the precipitate was filtered as crystals. Then, recrystallization from acetonitrile was conducted. The yield was 54.0 g (81.7%).

$[\alpha]_D^{18}$ −13.7° (c=1.04 CHCl$_3$).

Elemental analysis: As C$_{46}$H$_{59}$N$_5$O$_9$ Calculated: C, 66.89; H, 7.20; N, 8.48. Found: C, 66.69; H, 7.23; N, 8.31.

Boc-Leu-Asp(OBzl)-Ile-Ile-Trp-OBzl: In 210 ml of TFA containing 10% 1,2-ethanedithiol was dissolved 48.0 g of Boc-Asp(OBzl)-Ile-Ile-Trp-OBzl under ice cooling, and the resulting solution was allowed to stand at room temperature for 15 minutes. The solvent was removed therefrom by distillation and 14.5 ml of 4 N HCl-dioxane was added to the residue, followed by stirring. Then, diethyl ether was added thereto and the precipitate was filtered. This precipitate was dissolved in 300 ml of DMF and neutralized with 42 ml of TEA under ice cooling. Then, precipitated TEA.HCl was filtered off. To the filtrate was added 27.3 g of Boc-Leu-ONB and stirred overnight. After the solvent was removed by distillation under reduced pressure, 600 ml of CHCl$_3$ was added to the residue to dissolve it. The resulting solution was washed with 10% aqueous citric acid, 5% NaHCO$_3$ and water, and dried with anhydrous MgSO$_4$. After the solvent was distilled off under reduced pressure, petroleum ether was added to the residue and the precipitate was filtered. Then, recrystallization from hydrous acetonitrile was conducted. The yield was 53.1 g (97.5%).

$[\alpha]_D^{18}$ −20.6° (c=1.02 CHCl$_3$).

Elemental analysis: As C$_{52}$H$_{70}$N$_6$O$_{10}$.½H$_2$O Calculated: C, 65.87; H, 7.55; N, 8.86. Found: C, 66.08; H, 7.58; N, 8.78.

Boc-His-Leu-Asp(OBzl)-Ile-Ile-Trp-OBzl: In 220 ml of TFA containing 10% 1,2-ethanedithiol was dissolved 46.5 g of Boc-Leu-Asp(OBzl)-Ile-Ile-Trp-OBzl under ice cooling, and the resulting solution was allowed to stand at room temperature for 15 minutes. The solvent was removed therefrom by distillation under reduced pressure. Then, diethyl ether was added thereto and the precipitate was filtered. This precipitate was dissolved in 25 ml of DMF and 20 ml of TEA was added thereto, followed by stirring. Thereafter, diethyl ether was added thereto, and the precipitate was filtered as powder. Then, the powder was dissolved in 200 ml of DMF and Boc-His(Tos)-ONB prepared from 22.3 g of Boc-His(Tos)-OH, 11.7 g of HONB and 13.5 g of DCC was added thereto. The resulting solution was stirred overnight. After the solvent was distilled off, acetonitrile was added to the residue and the precipitated powder was filtered. The yield was 45.9 g (86.2%).

$[\alpha]_D^{18}$ −16.6° (c=1.0, DMF).

Elemental analysis: As C$_{58}$H$_{77}$N$_9$O$_{11}$.2.5H$_2$O Calculated: C, 62.13; H, 7.37; N, 11.24. Found: C, 62.25; H, 7.02; N, 11.03.

Boc-Cys(MeBzl)-His-Leu-Asp(OBzl)-Ile-Ile-Trp-OBzl: In 88 ml of TFA containing 10% 1,2-ethanedithiol was dissolved 17.2 g of Boc-His-Leu-Asp(OBzl)-Ile-Ile-Trp-OBzl under ice cooling, and the resulting solution was allowed to stand at room temperature for 15 minutes. The solvent was removed therefrom by distillation under reduced pressure. Then, ethyl ether was added to the residue and the precipitate was filtered as powder. This powder was dissolved in 25 ml of DMF and 25 ml of TEA was added thereto, followed by stirring. Thereafter, 500 ml of ethyl ether was added thereto, and the precipitate was filtered as powder. Then, the powder was dissolved in 40 ml of DMF and Boc-Cys(MeBzl)-ONB prepared from 5.72 g of Boc-Cys(MeBzl)-OH, 3.48 g of HONB and 4.00 g of DCC was added thereto. The resulting solution was stirred overnight. After the solvent was distilled off, acetonitrile was added to the residue and the precipitate was filtered as powder. The powder was further washed in hot acetonitrile, cooled to room temperature, and then filtered. The yield was 15.0 g (72.9%).

$[\alpha]_D^{18}$ −23.3° (c=1.02, DMF).

Elemental analysis: As C$_{69}$H$_{90}$N$_{10}$O$_{12}$S.3H$_2$O Calculated: C, 61.96; H, 7.23; N, 10.47; S, 2.40. Found: C, 62.24; H, 6.90; N, 10.49; S, 2.53.

H-Cys-His-Leu-Asp-Ile-Ile-Trp-OH: In 1 ml of TFA containing 10% 1,2-ethanedithiol was dissolved 100 mg of Boc-Cys(MeBzl)-His-Leu-Asp(OBzl)-Ile-Ile-Trp-OBzl under ice cooling, and the resulting solution was allowed to stand at room temperature for 15 minutes. After the solvent was removed therefrom by distillation under reduced pressure, ethyl ether was added to the residue and the precipitate was filtered as powder. After drying, the powder was treated with 5 ml of HF in the presence of 0.5 ml of m-cresol at 0° C. for 1 hour. After HF was removed therefrom under reduced pressure, diethyl ether was added to the residue and the precipitate was filtered as powder. Then, the powder was washed with water. This powder was dissolved in 60% acetic acid and applied on a Sephadex LH-,20 column filled with the same solvent. Fractions of 160 ml to 180 ml were collected and lyophilized. The yield was 23 mg (32.8%).

Anal. for amino acids: Asp 1.0(1), Cys 0.80(1), Ile 2.13(2), Leu 0.99(1), His 1.07(1) and Trp 0.67(1) Mean recovery 90.5%.

(B) Synthesis of H-Arg—His-Leu-Asp-Ile-Ile-Trp-OH (Similar to C-terminal Portion of Endothelin-3, with High Solubility)

In 5 ml of TFA containing 20% 1,2-ethanedithiol was dissolved 538 mg of Boc-His-Leu-Asp(OBzl)-Ile-Ile-Trp-OBzl under ice cooling and the resulting solution was allowed to stand at room temperature for 15 minutes. After 95 mg of pTsOH.H$_2$O was added thereto to dissolve it, the solvent was removed therefrom by distillation under reduced pressure. The residue was dissolved in 5 ml of DMF and neutralized by adding 0.75 ml of DMF containing 10% TEA thereto. Then, 60 mg of Boc-Arg(NO$_2$)-OH, 50 mg of HONB and 50 mg of WSCD.HCl were added thereto, and the mixture was stirred overnight. After the solvent was distilled off under reduced pressure, water was added to the residue and the precipitate was filtered. After drying, this precipitate was suspended in 10 ml of hot acetonitrile, cooled to room temperature, and then filtered. The yield was 0.5 g (78.3%).

With HF was treated 102 mg of the resulting product in the presence of 0.2 ml of anisole and 0.2 ml of 1,2-ethanedithiol at 0° C. for 60 minutes, and then HF was removed by distillation under reduced pressure. After washing with diethyl ether, the residue was dissolved in 6 ml of 50% acetic acid and applied on a Sephadex G-25 (2.5×90 cm) column filled with the same solvent to develop it. Fractions of 100 ml to 137 ml were collected and lyophilized. The yield was 20 mg (26.3%).

Anal. for amino acids: Asp 0.98(1), Ile 1.95(2), Leu 1.0(1), His 0.95(1), Arg 0.98(1) and Trp 0.72(1) Mean recovery 89.7%

2. Preparation of Immunogen

The condensation product of the polypeptide Cys His Leu Asp Ile Ile Trp obtained in 1(A) of this example and bovine serum albumin (hereinafter referred to as BSA for brevity) was prepared according to the maleimide cross-linking method to provide an immunogen.

Namely, 20 mg of BSA was dissolved in 1.4 ml of 0.1 M phosphate buffer (pH 7.0), and 100 μl of a DMF solution containing 2.6 mg of N-(γ-maleimidebutyryloxy) succinimide (hereinafter referred to as GMBS for brevity) was mixed therewith. The reaction was conducted at room temperature for 40 minutes. After the reaction was completed, the resulting product was fractionated on a Sephadex G-25 column previously equilibrated with 0.1 M phosphate buffer (pH 6.5) containing 2.5 mM ethylenediaminetetraacetic acid (EDTA). Then, 1.2 ml of the eluted fractions containing 5.4 mg of maleimide group-introduced BSA was, reacted with 1.8 mg of the polypeptide Cys His Leu Asp Ile Ile Trp dissolved or dispersed in 1.2 ml of 90% aqueous dimethyl sulfoxide, at 4° C. for 3 days. After the reaction was completed, the product was dialyzed against an isotonic sodium chloride solution at 4° C. for 2 days.

3. Immunization

An emulsion was prepared by adding 550 µl of Freund's complete adjuvant to 450 µl of an isotonic sodium chloride solution containing 600 µg of the immunogen obtained in 2 of this example, and mixing them thoroughly. Then, the emulsion was subcutaneously inoculated on each of the rabbits at about 20 spots. After 6 weeks from the inoculation, an emulsion similarly prepared by using Freund's incomplete adjuvant was subcutaneously inoculated on each of the rabbits. This operation was repeated 4 times at monthly intervals. After 7 days from the supplemental immunization, blood was partially collected from the rabbits and an antiserum was obtained by methods known in the art.

4. Preparation of affinity Solid Phase

The polypeptide Arg His Leu Asp Ile Ile Trp was directly bound to CNBr-activated Sepharose 4B to provide an affinity solid phase.

Namely, 1.5 mg of the polypeptide Arg His Leu Asp Ile Ile Trp was dissolved in 10 ml of 0.1 M sodium hydrogencarbonate solution containing 0.5 M NaCl and then reacted with 1 g of CNBr-activated Sepharose 4B at room temperature for 3 hours. After treatment with 0.1 M Tris-hydrochloric acid buffer (pH 8) to remove the unreacted active groups therefrom, the affinity solid phase thus prepared was dispersed in phosphate buffered saline (PBS) and stored at 4° C.

5. Purification of Anti-Endothelin-3 C-terminal Peptide Antibody by Affinity Solid Phase An antibody was partially purified from 16 ml of the rabbit antiserum obtained in 3 of this example, by the ammonium sulfate salt precipitation method. Namely, 10 ml of PBS was added to 10 ml of the antiserum, and 16.5 ml of a saturated ammonium sulfate solution was further added slowly thereto with stirring (to a final concentration of 45%). After standing for 30 minutes, the resulting mixture was centrifuged at 12,000×g for 20 minutes to form a precipitate. The precipitate was dissolved in 10 ml of PBS. Then, the saturated ammonium sulfate solution was similarly added thereto to give a final saturated concentration of 30%, followed by centrifugation. The precipitate thus formed was dissolved in 10 ml of 0.01 M borate buffer (pH 8, hereinafter referred to as BBS for brevity) containing 0.15 M NaCl. Then, the solution was dialyzed against 0.01 M phosphate buffer (pH 8, hereinafter referred to as buffer B) containing 0.01 M NaCl at 4° C. for 2 days. After dialysis against BBS, the antibody fractions were applied on a column (10 mm φ×40 mm) filled with the affinity solid phase described in 4 of this example. After thorough washing with BBS, a specific antibody was eluted with 0.1 M acetate buffer (pH 4.5) containing 0.1 M NaCl, and further with 0.05 M glycine-hydrochloric acid buffer (pH 2.0) containing 0.1 M NaCl.

After neutralization, the eluate was dialyzed against BBS. The specific antibody was observed in the fraction eluted at pH 2. From that fraction, 18 mg of a specific antibody was obtained.

6. Preparation of Horseradish Peroxidase (HRP)-Labeled Anti-Endothelin-3 C-Terminal Peptide Antibody A Fab'-HRP marker was prepared from the affinity-purified anti-Cys His Leu Asp Ile Ile Trp antibody described in 5 of this example according to the method of Ishikawa et al. [J. Appl Biochem., 6, 56-63 (1984)].

That is to say, 160 µg of pepsin (crystallized twice, Sigma) was added to 0.1 M acetate buffer (pH 4.5) in which 6.4 mg of the specific antibody was dissolved, followed by reaction at 37° C. for 16 hours. Then, the F(ab')$_2$ fractions were purified by FPLC(Pharmacia) using a Superrose 12 column equilibrated with BBS. After those fractions were dialyzed against 0.1 M acetate buffer (pH 5), β-mercaptoethylamine was added to a final concentration of 20 mM and the resulting solution was allowed to stand at 37° C. for 90 minutes. The reaction solution was separated by FPLC using a Superrose 12 column equilibrated with 0.1 M phosphate buffer (pH 6.0) containing 2.5 mM EDTA. Thus, the Fab' fraction was obtained.

On the other hand, 5 mg of horseradish peroxidase (HRP) was dissolved in 0.9 ml of 0.1 M phosphate buffer (pH 7), and 1.05 mg of GMBS dissolved in 50 µl of DMF was added thereto. The reaction was conducted at room temperature for 40 minutes.

The reaction solution was separated on a Sephadex G-25 column (eluent: 0.1 M phosphate buffer, pH 6.8), and 3.5 mg of maleimidated peroxidase obtained thereby was mixed with 0.8 mg of the above Fab' fraction. The resulting mixture was concentrated to about 0.3 ml by a collodion pack (Emuesu Kiki) and then allowed to stand at 4° C. for 16 hours. The reaction solution was applied on a Ultrogel AcA44 column (10 mm φ×40 mm) using 0.1 M phosphate buffer (pH 6.5) as an eluent to purify the Fab'-peroxidase conjugate fraction.

EXAMPLE 2

Preparation of Monoclonal Anti-Endothelin-3 Antibody

1. Preparation of Immunogen

Endothelin-3 was condensed with bovine thyroglobulin (hereinafter referred to as TG) by the maleimide crosslinking method to provide an immunogen.

Namely, 265 nmoles of endothelin-3 (purchased from Peptide Laboratory) was dissolved in 450 µl of 0.1 M phosphate buffer (pH 7.0, containing 10% DMF). The resulting solution was mixed with 50 µl of a DMF solution containing 6.6 µmoles of GMBS, followed by reaction at room temperature for 30 minutes.

On the other hand, 20 mg (40 nmoles) of TG was dissolved in 1.4 ml of 0.02 M phosphate buffer (pH 6.8) containing 0.15 M NaCl, and 100 µl, of a DMF solution containing 2.5 mg (8.0 µmoles) of N-succinimidyl-3-(2-pyridylthio) propionate (hereinafter referred to as SPDP for brevity) was mixed therewith, followed by reaction at room temperature for 40 minutes. After the reaction was completed, 0.5 ml of 0.1 M acetate buffer (pH 4.5) containing 12.4 mg (80 µmoles) of dithiothreitol was added thereto and the reaction was further conducted at room temperature for 20 minutes. Then, the resulting product was fractionated on a Sephadex G-25 column. Thus, 12 mg (24 nmoles) of SH group-introduced TG was obtained.

Subsequently, 190 TM nmoles of the maleimide group-introduced endothelin-3 and 5.9 nmoles of the SH group-introduced TG were mixed with each other and reacted at 4° C. for 2 days. Thereafter, the resulting product was dialyzed against an isotonic sodium chloride solution at 4° C. for 2 days.

2. Immunization

The female mice BALB/C 6 to 8 weeks old were subcutaneously immunized with 100 μg/mouse of the immunogen obtained in 1 of this example and Freund's complete adjuvant. Then, supplemental immunization was carried out 2 to 3 times at 3-week intervals.

3. Preparation of HRP-Labeled Endothelin-3

In 450 μl of 0.1 M phosphate buffer (pH 7.0) was dissolved 80 nmoles of endothelin-3, and 50 μl of a DMF solution containing 295 μg (2.0 μmoles) of GMBS was mixed therewith, followed by reaction at room temperature for 30 minutes. After the reaction was completed, the resulting product was fractionated on a Sephadex G-15 column. Thus, 60 nmoles of a maleimide group-introduced polypeptide was obtained.

On the other hand, 10 mg (250 nmoles) of HRP was dissolved in 1.4 ml of 0.02 M phosphate buffer (pH 6.8) containing 0.15 M NaCl, and 100 μl of a DMF solution containing 1.17 mg (3.75 μmoles) of N-succinimidyl 3-(2-pyridylthio)propionate (SPDP) was mixed therewith, followed by reaction at room temperature for 40 minutes. After the reaction was completed, 0.5 ml of 0.1 M acetate buffer (pH 4.5) containing 12.4 mg (80 μmoles) of dithiothreitol was added thereto and the reaction was further conducted at room temperature for 20 minutes. Then, the resulting product was fractionated on a Sephadex G-25 column. Thus, 6 mg (150 nmoles) of an SH group-introduced enzyme was obtained.

Then, 50 nmoles of maleimide group-introduced endothelin-3 and 20 nmoles of SH group-introduced peroxidase were mixed and reacted with each other at 4° C. for 16 hours. After the reaction was completed, the resulting product was fractionated on a Ultrogel AcA44 column (LKB-Pharmacia) to obtain peroxidase-labeled endothelin-3.

4. Cell Fusion

The mice which showed relatively high antibody titers were finally immunized by inoculating, in their veins 0.25 ml of an isotonic sodium chloride solution in which 240 μg of the immunogen was dissolved. The spleens were taken out of the mice after 3 days from the final immunization, pressed by a stainless mesh, filtered and floated in Eagle's minimum essential mediums (MEM), whereby a spleen cell-floating solution was obtained. As the cell for cell fusion, BALB/C mouse-derived myeloma cell Pe-X63.Ag8.U1 (P3U1) was used [*Current Topics in Microbiology and Immunology*, 81, 1 (1978)]. The cell fusion was carried out according to the original method [*Nature*, 256, 495 (1975)]. Namely, the spleen cells and P3U1 were washed 3 times with serum-free MEM, respectively, and mixed with each other so that the number ratio of the spleen cells to P3U1 reached 5 : 1. The mixture was centrifuged at 800 rpm for 15 minutes to precipitate the cells. After the supernatant was removed, the precipitate was lightly loosened, and 0.3 ml of 45% polyethylene glycol (PEG) 6000 (Kochlight) was added thereto. Then, the mixture was allowed to stand in a hot water bath at 37° C. for 7 minutes, whereby the fusion was performed. After the fusion was completed, MEM was added to the cells at a rate of 2 ml per minute. After the total amount of added MEM reached 12 ml, the supernatant was removed by centrifugation at 600 rpm for 15 minutes. This cell precipitate was floated in GIT medium (GIT-10FCS, Wako Junyaku) containing 10% fetal calf serum so that P3U1 was contained in an amount of $2 \times 10^6$ cells per ml. This was seeded in 120 wells of 24-well multi-dishes (Linbro) in an amount of 1 ml per well. After seeding, the cells were incubated in a 5% carbon dioxide incubator at 37° C. After 24 hours of incubation, 1 ml portions of GIT-10FCS medium (HAT medium) containing HAT ($1 \times 10^{-4}$ M hypoxanthine, $4 \times 10^{-7}$ M aminopterin and $1.6 \times 10^{-3}$ M thymidine) were added to each well to initiate HAT selective culture. HAT selective culture was continued by discarding 1 ml of old liquor and then supplying 1 ml of HAT medium 3, 6 and 9 days after the initiation of the culture. The proliferation of hybridoma cells were observed 9 to 14 days after the completion of the cell fusion. When the culture solution turned yellow (about $1 \times 10^5$ cells/ml), the supernatants were collected and the antibody titer thereof was determined by the EIA described below.

5. Screening of Hybridoma Cell

The titer of the antibody in a hybridoma culture supernatant were determined by two kinds of methods described below. In both of the methods, an anti-mouse immunoglobulin antibody-bound microtiter plate was used. This plate was prepared in the following manner. First, 100 μl of 0.1 M carbonate buffer (pH 9.6) containing 20 μg/ml of the anti-mouse immunoglobulin antibody (IgG fraction, Kappel) was poured into each well of a 96-well microtiter plate, and the plate was allowed to stand at 4° C. for 24 hours. Then, the plate was washed with PBS, and 300 μl of PBS containing 25% Blockace (Snow Brand Milk Products) was poured into each well to inactivate excess binding sites of the wells, followed by reaction at least 4° C. for 24 hours.

(A) Enzyme Immunoassay (EIA) Using HRP-Labeled Endothelin-3

To an anti-mouse immunoglobulin antibody-bound microtiter plate were added 50 μl of buffer E (pH 7.0, 0.02 M phosphate buffer containing 10% Blockace, 2 mg/ml BSA, 0.4 M NaCl, 2 mM EDTA and 0.1% NaN$_3$) and 50 μl of the hybridoma culture supernatant, followed by reaction at room temperature for 4 hours. After the reaction was completed, the plate was washed with PBS, and then 100 μl of the HRP-labeled endothelin-3 prepared in 3 of this example [diluted 100 times with buffer A (pH 7.0, 0.02 M phosphate buffer containing 1% BSA)] was added thereto, followed by reaction at 4° C. for 16 hours. After the reaction was completed, the plate was washed with PBS, and then 100 μl of 0.1 M citrate buffer (pH 5.5) containing 0.2% o-phenylenediamine and 0.02% hydrogen peroxide was poured into each well to determine the enzyme activity on the solid phase thus prepared, followed by reaction at room temperature for 10 minutes. After 100 μl of 4 N sulfuric acid was added thereto to terminate the reaction, the absorption at 492 nm was measured by a plate reader (MTP-32, Corona) to determine the antibody activity.

The supernatants of all of the 120 wells in which the proliferation of the cells was observed were thus examined. As a result, the strong antibody titer was detected in the wells of Nos. 5 and 93.

(B) EIA Using HRP-Labeled Endothel,in-3 C-Terminal Peptide Antibody

To an anti-mouse immunoglobulin antibody-bound microtiter plate were added 50 μl of buffer E, 50 μl of the hybridoma culture supernatant and 50 μl of buffer E containing 6 ng/ml of endothelin-3, followed by reaction at room temperature for 4 hours. The plate was washed with PBS, and then 100 μl of the HRP-labeled endothelin-3 C-terminal peptide antibody prepared in 6 of Example 1 [diluted 300 times with buffer C (pH 7.2, 0.02 M phosphate buffer containing 1% BSA, 0.4 M NaCl and 2 mM EDTA)] was added thereto, followed by reaction at 4° C. for 16 hours. Then, the plate was washed with PBS, and thereafter the enzyme activity on the solid phase was assayed by the method described in 5(A) of this example.

The supernatants of all of the 120 wells in which the proliferation of the cells was observed were thus examined. As a result, the strong antibody titer was detected in the well of No. 93.

6. Cloning

The hybridoma cells of the wells of Nos showed the positive antibody activity were cloned by the limiting dilution method. Namely, the hybridoma cells were floated in RPMI 1640-20FCS so as to be contained in an amount of 1.5 cells/ml and 0.2 ml portions thereof were poured into each well of a 96-well microtiter plate (Nunk). Upon pouring, the thymocytes of BALB/C mouse were added thereto as feeder cells so as to be, contained in an amount of $5 \times 10^5$ cells per well. After about one week, the proliferation of the cells was observed. The titer of the antibodies in the supernatants were examined by the EIA described in 5 of this example. As a result, the antibodies were produced in 8 clones of 41 clones for the hybridoma cells of No. 5, and 7 clones of 41 clones for the hybridoma cells of No. 93.

Giving attention to clone AET-30 obtained from No. 93-18 of these clones and monoclonal antibody AET-30a produced thereby, the following experiments were carried out.

7. Preparation of Large Amount of Monoclonal Antibody

Into a mouse to which 0.5 ml of mineral oil had been intraperitoneally administered or an untreated mouse (BALB/C), $1 \times 10^6$ to $3 \times 10^6$ cells/mouse of hybridoma AET-30 were intraperitoneally injected. After 10 to 30 days, the antibody-containing ascites was collected.

8. Purification of Monoclonal Antibody

A monoclonal antibody was purified by a protein-A column from the ascites obtained in 7 of this example. Namely, 8 ml of the ascites was diluted with the same amount of a binding buffer (pH 9.0, 1.5 M glycine buffer containing 3.5 M NaCl and 0.05% NaN ), and subjected to a protein-A Sepharose (Pharmacia) column which was pre-equilibrated with the binding buffer to elute a specific antibody with an eluting buffer (pH 3.0, 0.1 M citrate buffer containing 0.05% NaN ). By the above procedures, 40 mg of the specific antibody was obtained.

9. Determination of Class and Subclass of Monoclonal Antibody

Into each well of a 96-well microtiter plate was poured 100 µl of 0.1 M carbonate buffer (pH 9.6) containing 1 µg/ml of the purified monoclonal antibody obtained in 8 of this example, and the plate was allowed to stand at 4° C. for 24 hours. After the excess binding sites of the wells were blocked with Blockace in accordance with the method described in 5 of this example, the class and subclass of the monoclonal antibody were examined by the enzyme-linked immunosorbent assay (ELISA) using an isotype typing kit (Mouse-Typer TM Sub-Isotyping Kit, Bio RAD). As a result, it was found that AET-30a belonged to IgG1, κ class.

EXAMPLE 3

Competitive Method-EIA

To the anti-mouse immunoglobulin antibody-bound microtiter plate described in 5 of Example 2 were added 50 µl of an AET-30-containing culture supernatant diluted 75 times with buffer C and 50 µl of the standard solution of endothelin-1, followed by reaction at room temperature for 1 hour. Then, the HRP-labeled endothelin-3 described in 3 of Example 2 (diluted 100 times with buffer A) was added thereto, followed by reaction at 4° C. for 16 hours. After the reaction was completed, the plate was washed with PBS, and then the enzyme activity on the solid phase was assayed by the method described in 5(A) of Example 2.

The test was repeated under the same conditions as described above with the exception that the standard solution of endothelin-1 was substituted for the standard solution of endothelin-3.

Figure 1:
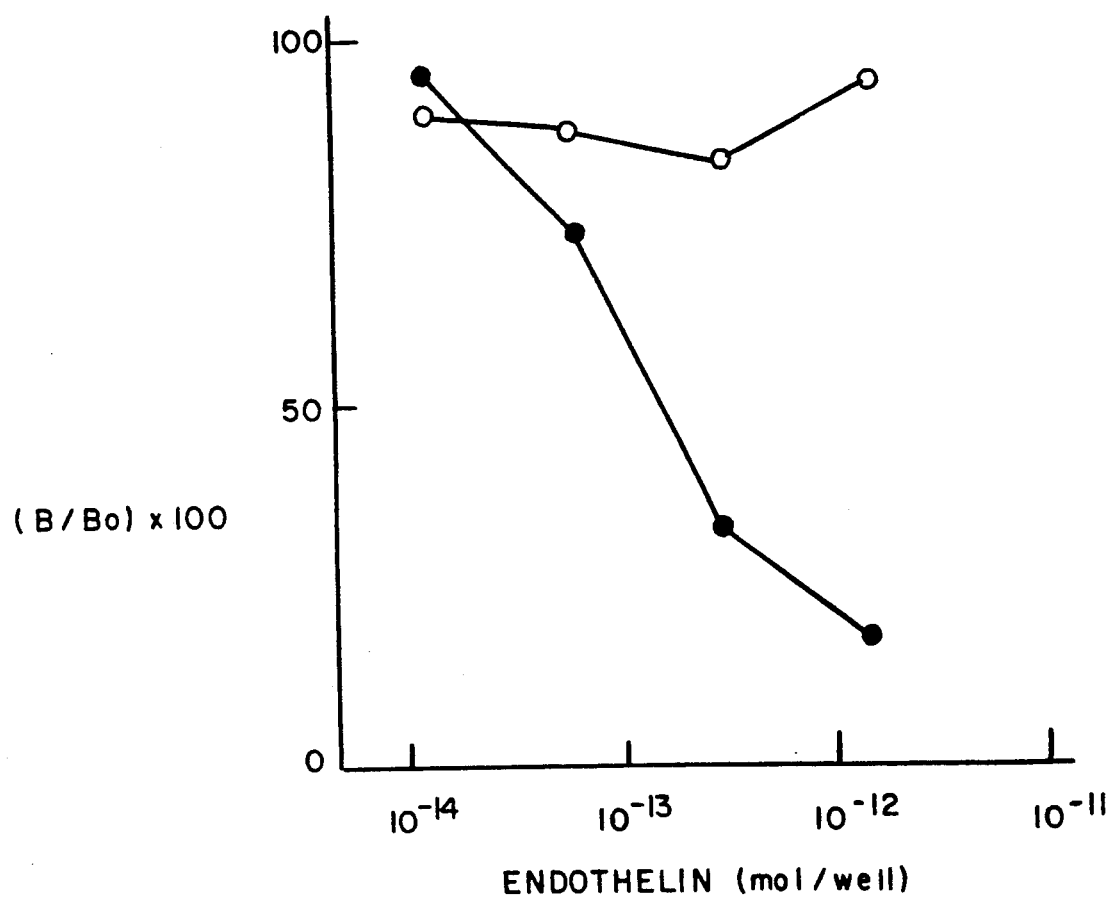

The results are shown in FIG. 1. In the drawing, -●- indicates the standard curve of endothelin-3, and -○- indicates the standard curve of endothelin-1. The results shown in FIG. 1 revealed that monoclonal antibody AET-30a reacted with endothelin-3, but did not react with endothelin-1.

EXAMPLE 4

Sandwich Method-EIA 0.1 M carbonate buffer (pH 9.6) containing 20 µg/ml of purified monoclonal antibody AET-30a was poured in an amount of 100 µl into each well of a 96-well microtiter plate, and the plate was allowed to stand 4° C. for 24 hours. The excess binding sites of the wells were inactivated by adding 300 µl of Blockace (manufactured by Snow Brand Milk Products and sold by Dainippon Pharmaceutical) diluted with PBS.

The standard solution of endothelin-3, endothelin-1, endothelin-2 (human), big endothelin-1 (human), big endothelin-1 (porcine) or big endothelin-3 (22-42) (human), which was diluted with buffer E, was added in an amount of 100 µl to each well of the microtiter plate prepared as described above, followed by reaction at 4° C. for 24 hours. After washing with PBS, 100 µl of the HRP-labeled endothelin-3 C-terminal peptide antibody prepared in 6 of Example 1 (diluted 300 times with buffer C) was added thereto, followed by reaction at 4° C. for 24 hours. After washing with PBS, the enzyme activity on the solid phase was assayed by the method described in 5(A) of Example 2.

Figure 2:
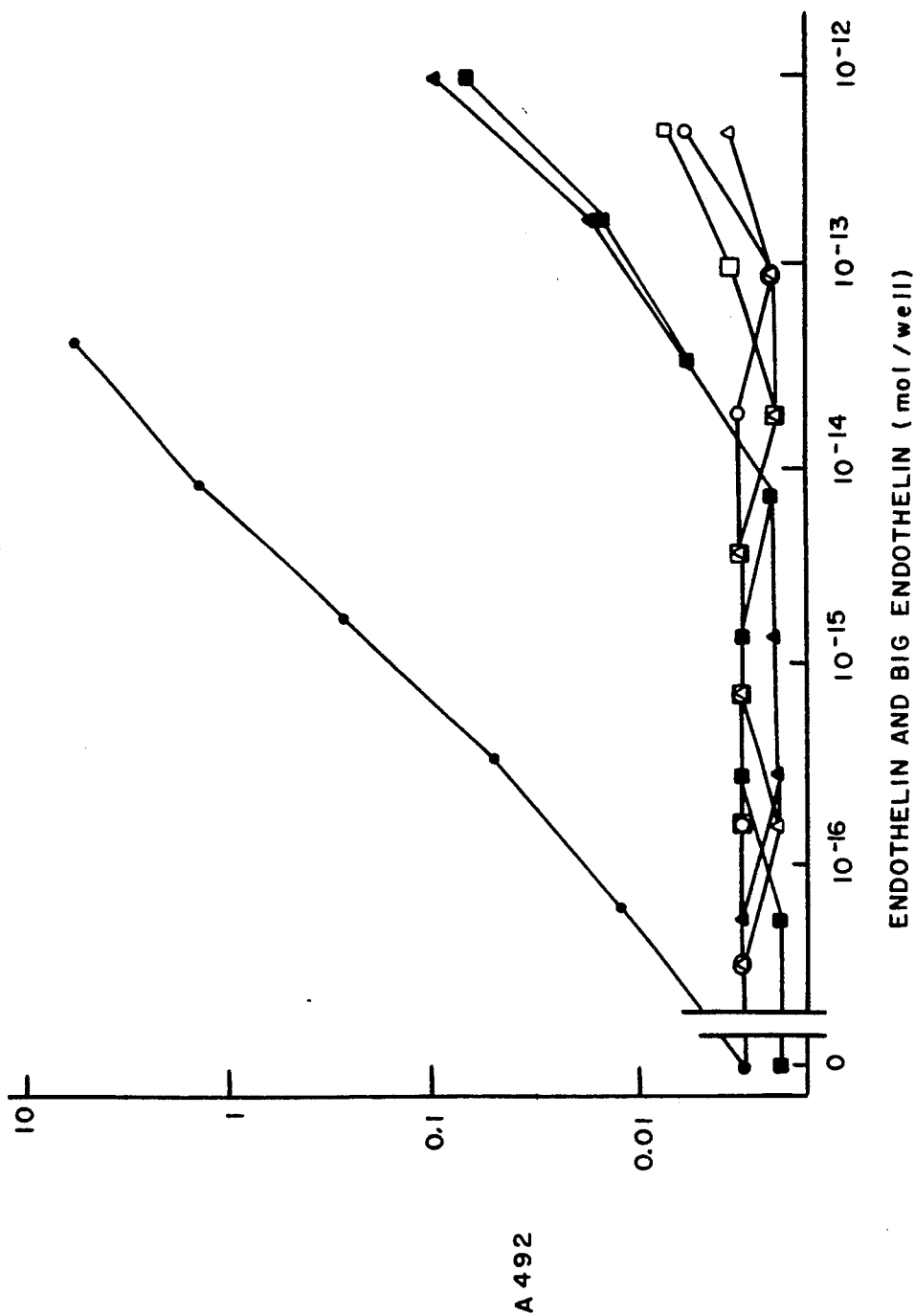
FIG. 2 is a graph showing standard curves of endothelin-3 (-●-), endothelin-1 (-▲-), endothelin-2 (-■-), human big endothelin-1 (-○-), porcine big endothelin-1 (-□-) and big endothelin-3 (-Δ-) obtained by the sandwich method-enzyme immunoas-say using monoclonal antibody AET-30a and anti-endothelin-3 C- terminal peptide antibody.

The results are shown in FIG. 2. In the drawing,-●- -▲-, -■-, -○-, -△- and -□- indicate the standard curves of endothelin-3, endothelin-1, endothelin-2 (human), big endothelin-1 (human), big endothelin-1 (porcine) and big endothelin-3 (human), respectively.

The results shown in FIG. 2 revealed that this assay was specific for endothelin-3, and that $4 \times 10^{-17}$ mole/-well of endothelin-3 could be detected with little reaction with other endothelins (the cross reactivity is 0.1% or less).

EXAMPLE 5

Preparation of Monoclonal Anti-Big Endothelin-3 C-Terminal Peptide Antibody

1. Synthesis of Peptides (A) Synthesis of big ET-3(22-42): H-Ile-Asn-Thr-Pro-Glu-Gln-Thr-Val-Pro-Tyr-Gly-Leu-Ser-Asn-Tyr-Arg-Gly-Ser-Phe-Arg-Gly-OH Big ET-3(22-42) was synthesized using 0.77 g (0.5 mmole) of a commercially available Boc-Gly-OCH$_2$-PAM resin (Applied Biosystems) and a peptide synthesizer (Model 430A, Applied Biosystems). The resin was treated with 50% trifluoroacetic acid/methylene chloride to deprotect a terminal amino group protected by a BOC group to a free amino group. The following protected amino acids were activated with 1-hydroxybenzotriazole/DCC (HOBt/DCC) and condensed to this free amino group in order according to the amino acid sequence of big ET-3(22-42): Boc-Arg(Tos), Boc-Phe, Boc-Ser(Bzl), Boc-Gly, Boc-Tyr(Br-Z), Boc-Asn, Boc-Leu, Boc-Pro, Boc-Val, Boc-Thr(Bzl), Boc-Gln, Boc-Glu(OBzl) and Boc-Ile.

The condensation was carried out again with the same amino acid derivatives activated with DCC or HOBt/DCC, and then unreacted amino groups were acetylated with acetic anhydride to obtain 0.86 g of a big ET-3(22-42)-OCH$_2$-PAM resin whose unreacted amino groups were protected.

0.35 g of this resin was treated with 5 ml of absolute hydrogen fluoride in the presence of 0.70 g of p-cresol at 0° C. for 60 minutes, followed by removal of hydrogen fluoride under reduced pressure. After washing with 5 ml of ethyl acetate twice, the residue was extracted with 5 ml of 50% aqueous acetic acid. The insoluble material was filtered off, followed by washing with 5 ml of 50% aqueous acetic acid. The filtrate and washings were combined and then concentrated to 2 to 3 ml under reduced pressure. The concentrated solution was subjected to a Sephadex LH-20 column (2×90 cm) to elute it with 50% acetic acid. Main fractions were collected, concentrated, and then dissolved in 100 ml of 0.1% aqueous trifluoroacetic acid. The resulting solution was subjected to a YMC-ODS AM120 S-50 resin column (2.6×7 cm), and elution was effected by a linear gradient of 0.1% aqueous trifluoroacetic acid to 50% acetonitrile (containing 0.1% trifluoroacetic acid). Main fractions were combined, and then lyophilized. Thus, 76 mg of white powder was obtained.

Anal. for amino acids: Asp 1.97(2), Thr 1.76(2), Ser 1.68(2), Glu 2.04(2), Gly 3.00(3), Val 1.00(1), Pro 1.90(2), Ile 0.95(1), Leu 0.99(1), Tyr 0.95(1), Phe 1.02(1), and Arg 2.27(2).

(M+H)$^+$ by mass spectrometry: 2356.16.
HPLC elution time: 17.01 minutes
Column conditions:
Column: YMC-ODS (AM-301, S-5 120A)
Eluent:
A (0.1% aqueous trifluoroacetic acid)
B (50% acetonitrile containing 0.1% trifluoroacetic acid)
A linear gradient elution from the eluent A to the eluent B for 50 minutes
Flow rate: 1.0 ml/min (B) Synthesis of big ET-3(1-42): H-Cys-Thr-Cys-Phe-Thr-Tyr-Lys-Asp-Lys-Glu-Cys-Val-Tyr-Tyr-Cys-His-Leu-Asp-Ile-Ile-Trp-Ile-Asn-Thr-Pro-Glu-Gln-Thr-Val-Pro-Tyr-Gly-Leu-Ser-Asn-Tyr-Arg-Gly-Ser-Phe-Arg-Gly-OH Big ET-3(1-42) was synthesized using 0.78 g (0.5 mmole) of a commercially available Boc-Gly-OCH$_2$-PAM resin (Applied Biosystems) and a peptide synthesizer (Model 430A, Applied Biosystems). The resin was treated with 50% trifluoroacetic acid/methylene chloride to deprotect a terminal amino group protected by a BOC group to a free amino group. The following protected amino acids were activated with HOBt/DCC and condensed to this free amino group in order according to the amino acid sequence of big ET-3(1-42): Boc-Arg(Tos), Boc-Phe, Boc-Ser(Bzl), Boc-Gly, Boc-Tyr(Br-z), Boc-Asn, Boc-Leu, Boc-Pro, Boc-Val, Boc-Thr(Bzl), Boc-Gln, Boc-Glu(OBzl), Boc-Ile, Boc-Trp(CHO), Boc-Asp(OBzl), Boc-His(DNP), Boc-Cys(-MeBzl) and Boc-Lys(Cl-Z).

The condensation was carried out again with the same amino acid derivatives activated with DCC or HOBt/DCC, and then unreacted amino groups were acetylated with acetic anhydride to obtain a big ET-3(1-42)-OCH$_2$-PAM resin whose unreacted amino groups were protected.

0.39 g of this resin was treated with 10 ml of absolute hydrogen fluoride in the presence of 0.74 g of p-cresol and 1.0 ml of 1,4-butanediol at 0° C. for 60 minutes, followed by removal of hydrogen fluoride under reduced pressure. After washing with 5 ml of ethyl acetate twice, the residue was extracted with 4 ml of trifluoroacetic acid. The insoluble material was filtered off, followed by washing with 2 ml of trifluoroacetic acid. The resulting solution was poured into 750 ml of 4 M aqueous urea, and the mixture was adjusted to pH 8.25 under ice cooling, followed by stirring overnight while gently blowing air therethrough. After a negative Ellman test was confirmed, the whole solution was subjected to a YMC-ODS AM120 S-50 resin column (2.6×7 cm), and elution was effected by a linear gradient of 0.1% aqueous trifluoroacetic acid to 50% acetonitrile (containing 0.1% trifluoroacetic acid). Main fractions were combined, and then lyophilized to obtain 16 mg of white powder. Using the same column, the powder was purified again by a linear gradient elution of 20% to 50%. Thus, 6.3 mg of a desired product was obtained.

Anal. for amino acids: Asp 3.84(4), Thr 3.31(4), Ser 2.02(2), Glu 3.04(3), Pro 2.22(2), Gly 3.31(3), Cys 1.20(2), Val 1.77(2), Ile 1.83(3), Leu 2.00(2), Tyr 4.64(5), Phe 1.92(2), Lys 1.78(2), His 0.88(1) and Arg 2.12(2).

(M+H)$^+$ by mass spectrometry: 4979.48.
HPLC elution time: 21.00 minutes.
Column conditions:
Column: YMC-ODS (AM-301, S-5 120A)
Eluent:
A (0.1% aqueous trifluoroacetic acid)
B (50% acetonitrile containing 0.1% trifluoroacetic acid)
A linear gradient elution from the eluent A to the eluent B for 50 minutes
Flow rate: 1.0 ml/min (C) Synthesis of big ET-3(22-41)-NH$_2$: H-Ile-Asn-Thr-Pro-Glu-Gln-Thr-Val-Pro-Tyr-Gly-Leu-Ser-Asn-Tyr-Arg-Gly-Ser-Phe-Arg-NH$_2$ Big ET-3(22-41)-NH$_2$ was synthesized using 0.60 g (0.5 mmole) of a commercially available p-methyl BHA resin (Applied Biosystems) and a peptide synthesizer (Model 430A, Applied Biosystems).

After Boc-Arg(Tos) was introduced in the resin with HOBt/DCC, the resin was treated with 50% trifluoroacetic acid/methylene chloride to deprotect a terminal amino group protected by a BOC group to a free amino group. The following protected amino acids were activated with HOBt/DCC and condensed to this free amino group in order according to the amino acid sequence of big ET-3(22-41)-NH₂: Boc-Phe, Boc-Ser(Bzl), Boc-Gly, Boc-Arg(Tos), Boc-Tyr(Br-z), Boc-Asn, Boc-Leu, Boc-Pro, Boc-Val, Boc-Thr(Bzl), Boc-Gln, Boc-Glu(OBzl) and Boc-Ile.

The condensation was carried out again with the same amino acid derivatives activated with DCC or HOBt/DCC, and then unreacted amino groups were acetylated with acetic anhydride to obtain 1.96 g of a big ET-3(22-41)-BHA resin whose unreacted amino groups were protected.

0.23 g of this resin was treated with 5 ml of absolute hydrogen fluoride in the presence of 0.40 g of p-cresol at 0° C. for 60 minutes, followed by removal of hydrogen fluoride under reduced pressure. After washing with 5 ml of ethyl acetate twice, the residue was extracted with 5 ml of 50% aqueous acetic acid. The insoluble material was filtered off, followed by washing with 5 ml of 50% aqueous acetic acid. The filtrate and washings were combined and then concentrated to 2 to 3 ml under reduced pressure. The concentrated solution was subjected to a Sephadex LH-20 column (2×90 cm) to elute it with 50% acetic Acid. Main fractions were collected, concentrated, and then dissolved in 100 ml of 0.1% aqueous trifluoroacetic acid. The resulting solution was subjected to a YMC-ODS AM120 S-50 resin column (2.6×7 cm), and elution was effected by a linear gradient of 0.1% aqueous trifluoroacetic acid to 50% acetonitrile (containing 0.1% trifluoroacetic acid). Main fractions were combined, and then lyophilized. Thus, 56 mg of white powder was obtained.

Anal. for amino acids: Asp 1.97(2), Thr 1.88(2), Ser 1.75(2), Glu 2.05(2), Gly 3.00(3), Val 1.00(1), Pro 1.93(2), Ile 0.95(1), Leu 0.98(1), Tyr 0.95(1), Phe 1.02(1) and Arg 2.18(2).

(M+H)⁺ by mass spectrometry: 2298.19.
HPLC elution time: 17.01 minutes.
Column conditions:
Column: YMC-ODS (AM-301, S-5 120A)
Eluent:
  A (0.1% aqueous trifluoroacetic acid)
  B (50% acetonitrile containing 0.1% trifluoroacetic acid)
A linear gradient elution from the eluent A to the eluent B for 50 minutes
Flow rate: 1.0 ml/min (D) Synthesis of big ET-3(1-41)-NH₂: H-Cys-Thr-Cys-Phe-Thr-Tyr-Lys-Asp-Lys-Glu-Cys-Val-Tyr-Tyr-Cys-His-Leu-Asp-Ile-Ile-Trp-Ile-Asn-Thr-Pro-Glu-Gln-Thr-Val-Pro-Tyr-Gly-Leu-Ser-Asn-Tyr-Arg-Gly-Ser-Phe-Arg-NH₂

Big ET-3(1-42)-NH₂ was synthesized using 0.60 g (0.5 mmole) of a commercially available p-methyl BHA resin (Applied Biosystems) and a peptide synthesizer (Model 430A, Applied Biosystems).

After Boc-Arg(Tos) was introduced in the resin with HOBt/DCC, the resin was treated with 50% trifluoroacetic acid/methylene chloride to deprotect a terminal amino group protected by a BOC group to a free amino group. The following protected amino acids were activated with HOBt/DCC and condensed to this free amino group in order according to the amino acid sequence of big ET-3(1-42)-NH₂: Boc-Phe, Boc-Ser(Bzl), Boc-Gly, Boc-Arg(Tos), Boc-Tyr(Br-Z), Boc-Asn, Boc-Leu, Boc-Pro, Boc-Val, Boc-Thr(Bzl), Boc-Gln, Boc-Glu(OBzl), Boc-Ile, Boc-Trp(CHO), Boc-Asp(OBzl), Boc-His(DNP), Boc-Cys(MeBzl) and Boc-Lys(Cl-Z).

The condensation was carried out again with the same amino acid derivatives activated with DCC or HOBt/DCC, and then unreacted amino groups were acetylated with acetic anhydride to obtain a big ET-3(1-42)-BHA resin whose unreacted amino groups were protected. The resulting resin was suspended in 20 ml of N,N'-dimethylformamide, and 2 ml of thiophenol was added thereto, followed by gentle stirring at room temperature for 2 hours. Then, the resin was filtered on a glass filter and washed with N,N'-dimethylformamide and dichloromethane, followed by drying to obtain 1.34 g of the resin.

0.74 g of this resin was treated with 10 ml of absolute hydrogen fluoride in the presence of 1.0 g of p-cresol and 1.0 ml of 1,4-butanediol at 0° C. for 60 minutes, followed by removal of hydrogen fluoride under reduced pressure. After washing with 5 ml of ethyl ether twice, the residue was extracted with 6 ml of trifluoroacetic acid. The insoluble material was filtered off, followed by washing with 2 ml of trifluoroacetic acid twice. The resulting solution was poured into 1,000 ml of 4 M aqueous urea, and the mixture was adjusted to pH 8.0 under ice cooling, followed by stirring overnight while gently blowing air therethrough. After a negative Ellman test was confirmed, the whole solution was subjected to a YMC-ODS AM120 S-50 resin column (2.6×7 cm), and elution was effected by a linear gradient of 0.1% aqueous trifluoroacetic acid to 50% acetonitrile (containing 0.1% trifluoroacetic acid). Main fractions were combined, and then lyophilized to obtain 35 mg of white powder. Using the same column, the powder was purified again by a linear gradient elution of 20% to 50%. Thus, 9.5 mg of a desired product was obtained.

Anal. for amino acids: Asp 3.84(4), Thr 3.81(4), Ser 1.98(2), Glu 3.04(3), Pro 2.09(2), Gly 3.30(3), Cys 1.60(2), Val 1.79(2), Ile 1.83(3), Leu 2.00(2), Tyr 4.72(5), Phe 1.92(2), Lys 1.88(2), His 0.91(1) and Arg 2.20(2).

(M+H)⁺ by mass spectrometry: 4921.31.
HPLC elution time: 21.00 minutes.
Column conditions:
Column: YMC-ODS (AM-301, S-5 120A)
Eluent:
  A (0.1% aqueous trifluoroacetic acid)
  B (50% acetonitrile containing 0.1% trifluoroacetic acid)
A linear gradient elution from the eluent A to the eluent B for 50 minutes
Flow rate: 1.0 ml/min 2. Preparation of Immunogen The big endothelin-3 C-terminal peptide Ile Asn Thr Pro Glu Gln Thr Val Pro Tyr Gly Leu Ser Asn Tyr Arg Gly Ser Phe Arg Gly which was obtained in 1(1) of this example was condensed with TG by the maleimide cross-linking method described below to provide an immunogen.

Namely, 1.28 μmoles of the polypeptide was dissolved in 350 μl of 0.1 M phosphate buffer (pH 7.0, containing 10% DMF). The resulting solution was mixed with 100 μl of a DMF solution containing 25.6 μmoles of GMBS, followed by reaction at room temperature for 30 minutes.

On the other hand, 30 mg (60 nmoles) of TG was dissolved in 1.4 ml of 0.02 M phosphate buffer (pH 6.8) containing 0.15 M NaCl, and a DMF solution containing 3.7 mg (12.0 μmoles) of SPDP was mixed therewith, followed by reaction at room temperature for 40 minutes. After the reaction was completed, 0.5 ml of 0.1 M acetate buffer (pH 4.5) containing 18.6 mg (120 μmoles) of dithiothreitol was added thereto and the reaction was further conducted at room temperature for 20 minutes. Then, the resulting product was fractionated on a Sephadex G-25 column to obtain 18 mg (36 nmoles) of SH group-introduced TG.

Subsequently, 920 nmoles of the maleimide group-introduced polypeptide and 29 nmoles of the SH group-introduced TG were mixed with each other and reacted at 4° C. for 2 days. Thereafter, the resulting product was dialyzed against an isotonic sodium chloride solution at 4° C. for 2 days.

3. Immunization

The female mice BALB/C 6 to 8 weeks old were subcutaneously immunized with 15 μg/mouse of the immunogen obtained in 2 of this example and Freund's complete adjuvant Then, supplemental immunization was carried out twice at 3-week intervals.

4. Preparation of HRP-Labeled Big Endothelin-3 C-Terminal Peptide

In 500 μl of 0.1 M phosphate buffer (pH 7.0) was dissolved 330 nmoles of the big endothelin-3 C-terminal peptide, and 50 μl of a DMF solution containing 2.78 mg (9.9 μmoles) of GMBS was mixed therewith, followed by reaction at room temperature for 30 minutes. After the reaction was completed, the resulting product was fractionated on a Sephadex G-15 column to obtain 200 nmoles of a maleimide group-introduced polypeptide.

On the other hand, using 10 mg (250 nmoles) of HRP, 6 mg (150 nmoles) of an SH group-introduced enzyme was obtained in accordance with the method describe in 3 of Example 2.

Then, 200 nmoles of the maleimide group-introduced big endothelin-3 c-terminal peptide and 50 nmoles of SH group-introduced peroxidase were mixed and reacted with each other at 4° C. for 16 hours. After the reaction was completed, the resulting product was fractionated on a Ultrogel AcA44 column (LKB-Pharmacia) to obtain a peroxidase-labeled big endothelin-3 C-terminal peptide.

5. Cell Fusion

For the big endothelin-3 C-terminal peptide described in 3 of this example, cell fusion was performed in accordance with the method described in 4 of Example 2 using the immunized mice to obtain hybridoma cells.

6. Screening of Hybridoma Cell

The titer of the antibody in a hybridoma culture supernatant were determined by two kinds of methods described below. Namely, an anti-mouse immunoglobulin 10 antibody-bound or big endothelin-3,C-terminal peptide-bound microtiter plate was used. This plate was prepared in the following manner. First, 100 μl of 0.1 M carbonate buffer (pH 9.6) containing 20 μg/ml of the anti-mouse immunoglobulin antibody (IgG fraction, Kappel) or the big endothelin-3 C-terminal peptide was poured into each well of a 96-well microtiter plate, and the plate was allowed to stand at 4° C. for 24 hours. Then, the plate was washed with PBS, and 300 μl of PBS containing 25% Blockace (Snow Brand Milk Products) was poured into each well to inactivate excess binding sites of the wells, followed by reaction at least 4° C. for 24 hours.

(A) EIA Using HRP-Labeled Big Endothelin-3 C-Terminal Peptide

To an anti-mouse immunoglobulin antibody-bound microtiter plate were added 50 μl of buffer E (pH 7.0, 0.02 M phosphate buffer containing 10% Blockace, 2 mg/ml BSA, 0.4 M NaCl, 2 mM EDTA and 0.1% NaN$_3$) and 50 μl of the hybridoma culture supernatant, followed by reaction at room temperature for 4 hours. After the reaction was completed, 100 μl of the HRP-labeled big endothelin-3 C-terminal peptide prepared in 4 of this example (diluted 400 times with buffer C) was added thereto, followed by reaction at 4° C. for 16 hours. After the reaction was completed, the plate was washed with PBS, and then the enzyme activity on the solid phase was assayed in accordance with the method described in 5(A) of Example 2.

The supernatants of all of the 120 wells in which the proliferation of the cells was observed were thus examined. As a result, the strong antibody titer was detected in the wells of Nos. 44 and 77.

(B) EIA Using Big Endothelin-3 C-Terminal Peptide-Bound Microtiter Plate

To a big endothelin-3 C-terminal peptide-bound microtiter plate were added 50 μl of buffer E and 100 μl of the hybridoma supernatant, followed by reaction at room temperature for 4 hours. After the reaction was completed, the plate was washed with PBS, and then 100 μl of the HRP-labeled anti-mouse immunoglobulin antibody (diluted 10,000 times with buffer C) was added thereto, followed by reaction at 4° C. for 16 hours. Then, the plate was washed with PBS, and thereafter the enzyme activity on the solid phase was assayed by the method described in 6(A) of this example.

The supernatants of all of the 120 wells in which the proliferation of the cells was observed were thus examined. As a result, the strong antibody titer was detected in the well of No. 77.

7. Cloning

The hybridoma cells of the wells of Nos. 44 and 77 which showed the positive antibody activity were cloned in accordance with the method described in 6 of Example 2. After about one week, the proliferation of the cells was observed. The titer of the antibodies in the supernatants were examined by the EIA described in 6(A) of this example. As a result, the antibodies were produced in 27 clones of 767 clones for the hybridoma cells of No. 44, and 75 clones of 76 clones for the hybridoma cells of No. 77.

Giving attention to clone bET-31 obtained from No. 77-30 of these clones and monoclonal antibody bET-31a produced thereby, and clone bET-23 obtained from No. 44-52 and monoclonal antibody bET-23a produced thereby, the following experiments were carried out.

8. Preparation of Large Amount of Monoclonal Antibody

Into a mouse to which 0.5 ml of mineral oil had been intraperitoneally administered or an untreated mouse (BALB/C), $1 \times 10^{-6}$ to $3 \times 10^6$ cells/mouse of hybridoma bET-31 or bET-23 were intraperitoneally injected. After 10 to 14 days, the antibody-containing ascites was collected.

9. Purification of Monoclonal Antibody

Each of monoclonal antibodies bET-31a and bET-23a was purified in accordance with the method described in 8 of Example 2 by a protein-A column from the ascites obtained in 7 of this example. Consequently, 30 mg of specific antibody bET-31a and 50 mg of specific antibody bET-23a was obtained. 10. Determination of Class and Subclass of Monoclonal Antibody The class and subclass of monoclonal antibodies bET-31a and bET-23a purified in 9 of this example were determined in accordance with the assay described in 9 of Example 2. As a result, it was found that both of bET-31a and bET-23a belonged to IgGl, κclass.

EXAMPLE 6

Competitive Method with Respect to Big Endothelin-3-EIA

To the anti-mouse immunoglobulin antibody-bound microtiter plate described in 6 of Example 5 were added 50 μl of a bET-30-containing or bET-containing culture supernatant diluted 100 times with buffer C and 50 μl of the standard solution of big endothelin-1, endothelin-3, big endothelin-3, big endothelin-3 C-terminal peptide (22-42) or big endothelin-3 C-terminal peptide (22-41)-NH$_2$, followed by reaction at room temperature for 1 hour. Then, the HRP-labeled big endothelin-3 C-terminal peptide described in 4 of Example 5 (diluted 200 times with buffer C) was added thereto, followed by reaction at 4° C. for 16 hours. After the reaction was completed, the plate was washed with PBS, and then the enzyme activity on the solid phase was assayed by the method described in 5(A) of Example 2.

Figure 3:
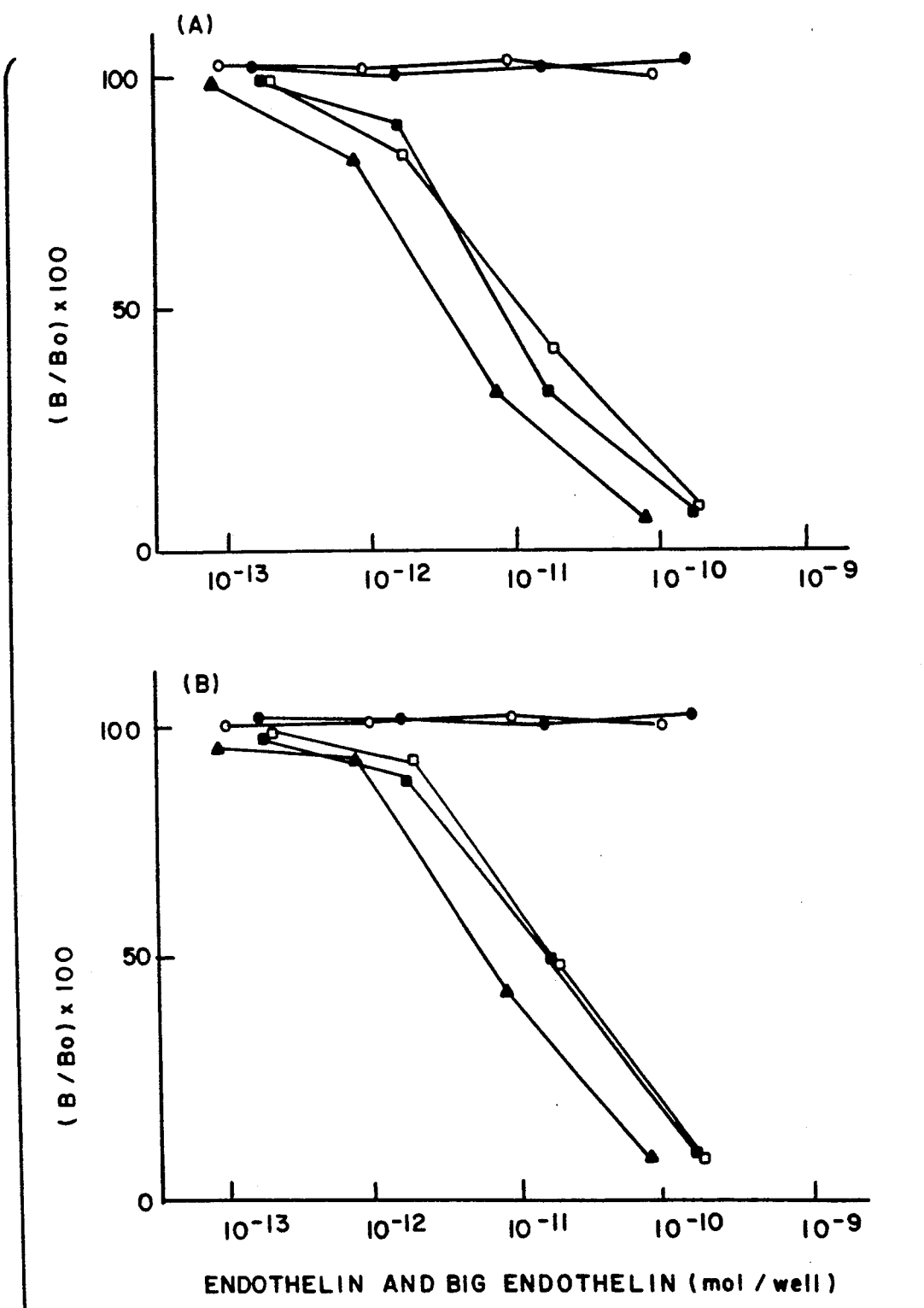

The results are shown in FIGS. 3(A) and 3(B). In the drawings, -▲-, -○-, -●-, -■- and -□- indicate the standard curves of big endothelin-3, big endothelin-1, endothelin-3, big endothelin-3 C-terminal peptide (22042) and big endothelin-3 C-terminal peptide (22–41)-NH$_2$, respectively. FIG. 3(A) shows the results for bET31a and FIG. 3(B) shows the results for bET23a. The results shown in FIGS. 3(A) and 3(B) revealed that both of bET-31a and bET-23a were antibodies specific for big endothelin-3 from the fact that they did not react with big endothelin-1 and endothelin-3, and that they had wide specificity for the C-terminal site of endothelin-3 from the fact that, they reacted with big endothelin-3 C-terminal peptide (22–42) and big endothelin-3 C-terminal peptide (22–41)-NH$_2$ to a similar degree.

EXAMPLE 7

Sandwich Method with Respect to Big Endothelin-3-EIA

1. Preparation of HRP-Labeled Monoclonal Antibody bET31a

A Fab'-HRP marker was prepared in accordance with the method described in 6 of Example 1 from bET-31a purified by the method described in 9 of Example 5.

That is to say, 317 μg of pepsin (crystallized twice, Sigma) was added to 0.1 M acetate buffer (pH 4.5) in which 10.5 mg of monoclonal antibody bET-31a was dissolved, followed by reaction at 37° C. for 16 hours. Then, the F(ab')$_2$ fractions were purified on a Ultrogel AcA44 column equilibrated with BBS. After those fractions were dialyzed against 0.1 M acetate buffer (pH 5), β-mercaptoethylamine was added to a final concentration of 20 mM and the resulting solution was allowed to stand at 37° C. for 90 minutes. The reaction solution was separated on a Sephadex G-25 column equilibrated with 0.1 M phosphate buffer (pH 6.0) containing 2.5 mM EDTA to obtain the Fab' fraction.

On the other hand, 5 mg of horseradish peroxidase was dissolved in 0.9 ml of 0.1 M phosphate buffer (pH 7), and 1.05 mg of GMBS dissolved in 50 μl of DMF was added thereto. The reaction was conducted at room temperature for 40 minutes.

The reaction solution was separated on a Sephadex G-25 column (eluent: 0.1 M phosphate buffer, pH 6.8), and 3.5 mg of maleimidated peroxidase obtained thereby was mixed with 1.3 mg of the above Fab' fraction. The resulting mixture was concentrated to about 0.3 ml by a collodion pack (Emuesu Kiki) and then allowed to stand at 4° C. for 16 hours. The reaction solution was applied on a Ultrogel AcA44 column (10 mm φ×40 mm) using 0.1 M phosphate buffer (pH 6.5) as an eluent to purify the Fab'-peroxidase conjugate fraction.

2. Preparation of HRP-Labeled Monoclonal Antibody bET-23a

Using 12.7 mg of monoclonal antibody bET-23a, HRP-labeled monoclonal antibody bET-23a was prepared in accordance with the method described in 1 of this example.

3. Sandwich Method-EIA

The standard solution of big endothelin-3, big endothelin-1 (human), endothelin-3, endothelin-1 or endothelin-2 (human), which was diluted with buffer E, was added in an amount of 100 μl to each well of the AET-30a-bound microtiter plate prepared in Example 4, followed by reaction at 4° C. for 24 hours. After washing with PBS, 100 μl of HRP-labeled monoclonal antibody bET-31a or bET-23a prepared in 1 or 2, respectively, of this example (diluted 200 times with buffer C) was added thereto, followed by reaction at 4° C. for 24 hours. After washing with PBS, the enzyme activity on the solid phase was assayed by the method described in 5(A) of Example 2.

Figure 4:
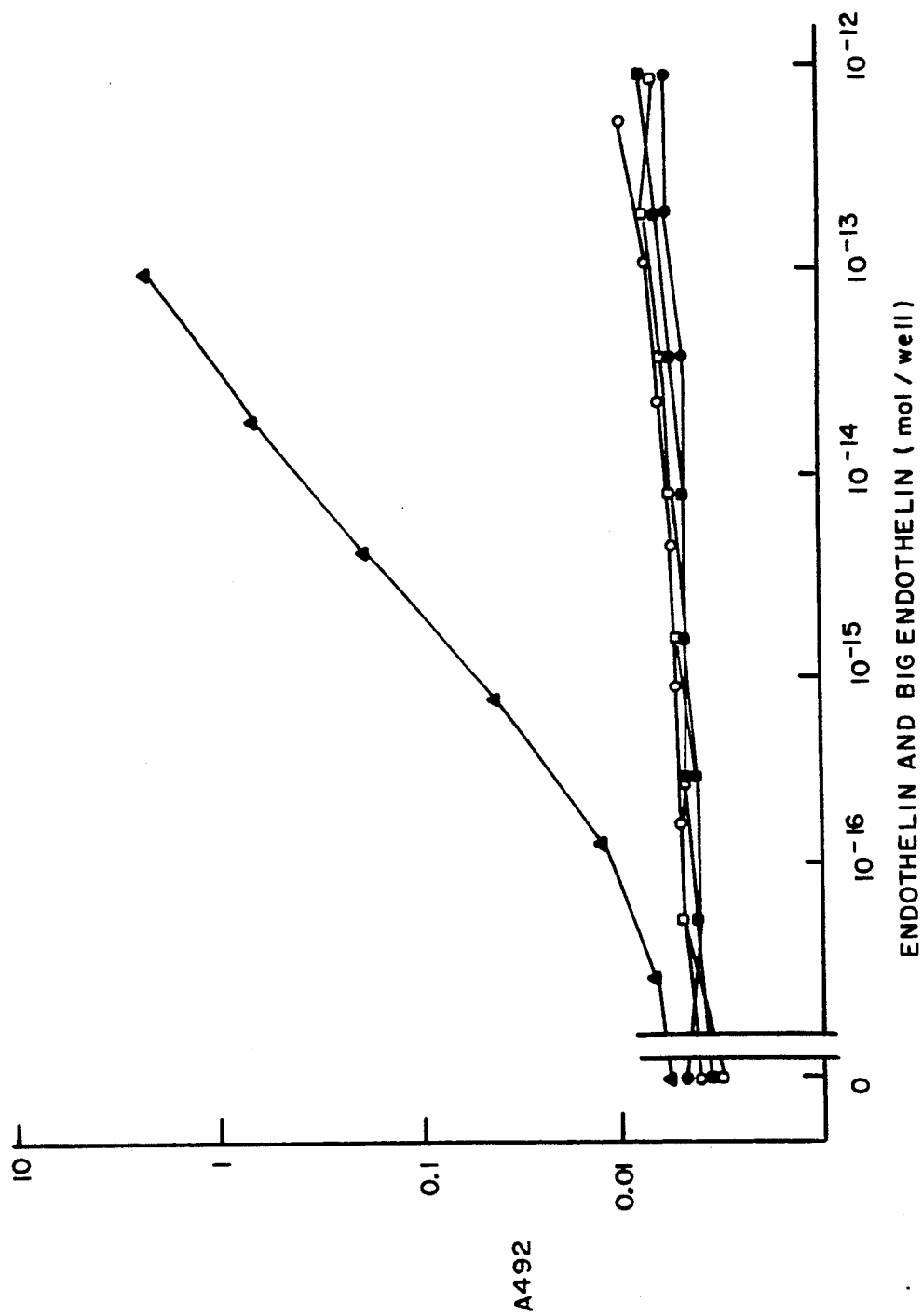
Figure 5:
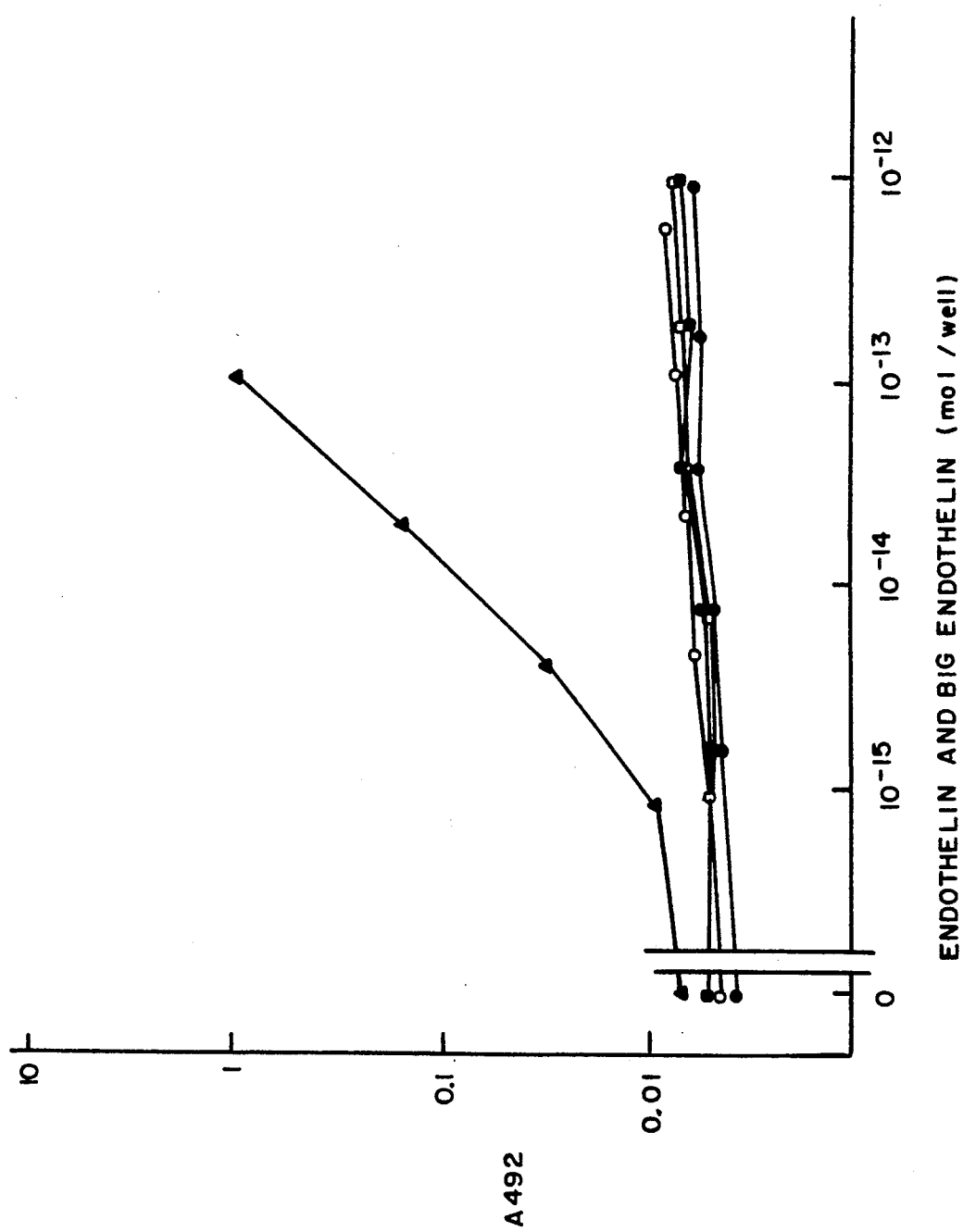

FIG. 4 shows the results obtained when HRP-labeled antibody bET-31a was used, and FIG. 5 shows the results obtained when HRP-labeled antibody bET-23a was used. In the drawing, -▲-, -○-, -●-, -■- and -□- indicate the standard curves of big endothelin-3, big endothelin-1 (human), endothelin-3, endothelin-1 and endothelin-2, respectively.

The results shown in FIG. 4 revealed that this assay using HRP-labeled antibody bET-31a was specific for big endothelin-3, and that HRP-labeled antibody bET-31a scarcely reacted with other endothelins (the cross reactivity is 0.1% or less). The measurement sensitivity was 6×10$^{-17}$ mole/well.

Similarly, the results shown in FIG. 5 revealed that this assay using HRP-labeled antibody bET-23a was specific for big endothelin-3, and that HRP-labeled antibody bET-23a scarcely reacted with other endothelins (the cross reactivity is 0.1% or less). The measurement sensitivity was 8×10$^{-16}$ mole/well.

EXAMPLE 8

Assay of Endothelin-3 in Amniotic Fluid

After 1 ml of amniotic fluid was concentrated and pre-treated with a Seppak C-18 cartridge, endothelin-3 in the amniotic fluid was assayed by the sandwich method-EIA described in Example 4. A method for pre-treating the amniotic fluid is shown in Scheme 1, and the results of assay are shown in Table 1. The results shown in Table 1 revealed that 4.2±3.9 pg/ml (mean+SD, n=8) of endothelin-3 existed in the amniotic fluid at birth.

EXAMPLE 9

Detection of Endothelin-3 in Amniotic Fluid by Reverse-Phase High Performance Liquid Chromatography (RP-HPLC)

1.5 ml of the amniotic fluid of No. 3 in Table 1 was pre-treated by using the Seppak C-18 cartridge described in Example 5, and then concentrated in a stream of nitrogen. The concentrate was dissolved in 100 μl of eluent A described later, followed by separation by RP-HPLC. The conditions of separation are as follows:

Column: ODS-80TM (4.6 mm φ×250 mm, Toso).

Eluent A: 5% acetonitrile containing 0.05% trifluoroacetic acid (TFA)

Eluent B: 60% acetonitrile containing 0.05% TFA.

Method of elution: The concentration of eluent B is linearly increased to 0 to 40% for the first 5 minutes, to 40 to 65% for the next 20 minutes, and to 65 to 100% for the further next 5 minutes.

Flow rate: 1 ml/min.

Fractionation: 0.5 ml/tube.

Figure 6:
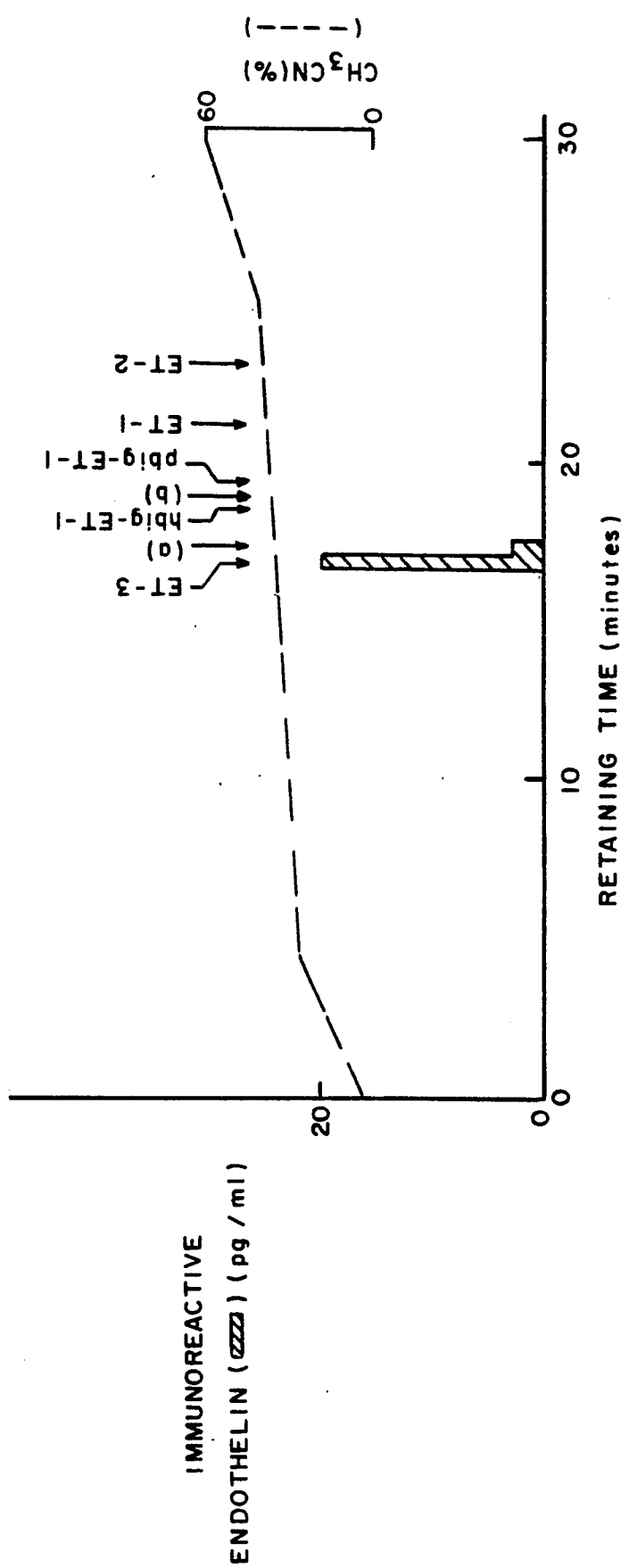
FIG. 6 is a graph showing the results detected by separation of human amniptic fluid treated with a Seppack C-18 cartridge by reverse-phase HPLC, and by the above sandwich method-enzyme immunoassay, wherein the arrows indicate elution positions of synthetic standard endothelins and big endothelins and the abbreviations are as follows.

The eluted fractions were concentrated to dryness by centrifugation under reduced pressure, and then dissolved in 250 μl of buffer E. The resulting solution was subjected to the sandwich method-EIA described in Example 4. The results are shown in FIG. 6. From the fact that the immunological activity of endothelin-3 in the amniotic fluid was detected at the elution position of synthetic endothelin-3, it was confirmed that the sandwich method-EIA detected endothelin-3.

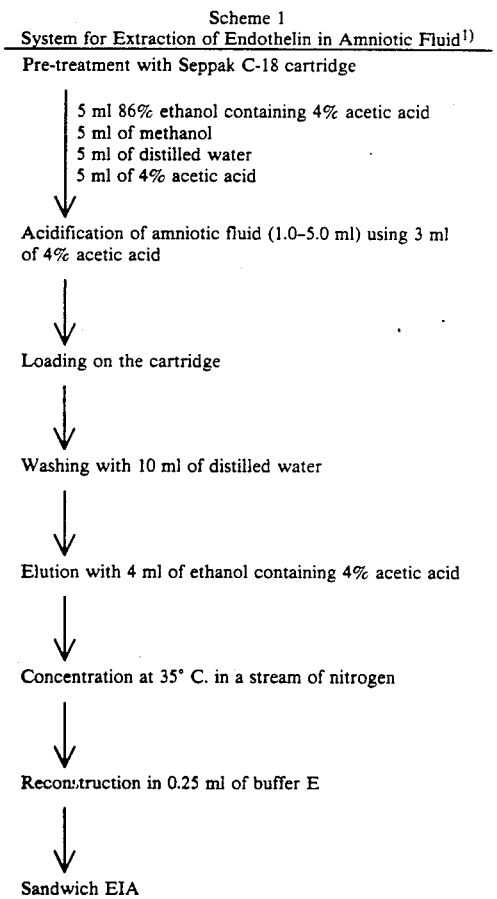

Scheme 1
System for Extraction of Endothelin in Amniotic Fluid[1])
Pre-treatment with Seppak C-18 cartridge 5 ml 86% ethanol containing 4% acetic acid
5 ml of methanol
5 ml of distilled water
5 ml of 4% acetic acid Acidification of amniotic fluid (1.0–5.0 ml) using 3 ml of 4% acetic acid Loading on the cartridge Washing with 10 ml of distilled water Elution with 4 ml of ethanol containing 4% acetic acid Concentration at 35° C. in a stream of nitrogen Reconstruction in 0.25 ml of buffer E Sandwich EIA

[1])F. Rosmalen et al., Clinic Chimica Acta, 331–340 (1987)

TABLE 1

| Assay of Endothelin-3 in Amniotic Fluid | |
|---|---|
| No. of Amniotic Fluid | Immunologically Reactive Endothelin-3 (pg/ml) |
| 1 | 4.3 |
| 2 | <0.5 |
| 3 | 13.3 |
| 4 | 2.6 |

TABLE 1-continued

| Assay of Endothelin-3 in Amniotic Fluid | |
|---|---|
| No. of Amniotic Fluid | Immunologically Reactive Endothelin-3 (pg/ml) |
| 5 | 3.3 |
| 6 | 4.3 |
| 7 | 2.2 |
| 8 | 3.2 |
| Mean ± SD | 4.2 ± 3.9 |

SD: Standard deviation

EXAMPLE 10

Assay of Endothelin-3 in Sera of Healthy Volunteers and Patients Undergoing Haemodialysis A human serum (1 ml) was concentrated and pretreated by the method shown in Scheme 1, followed by assay of endothelin-3 in accordance with the sandwich method-EIA described in Example 4. FIG. 7 shows the results of assay for the sera of 17 healthy volunteers (males, 37.5±4.9 years old) and 24 patients undergoing haemodialysis (males, 46.0±7.0 years old).

These results revealed that endothelin-3 in the sera could be determined by this assay, and that this assay was also clinically useful because the serum level of endothelin-3 increased in the patients undergoing haemodialysis.

EXAMPLE 11

Figure 8:
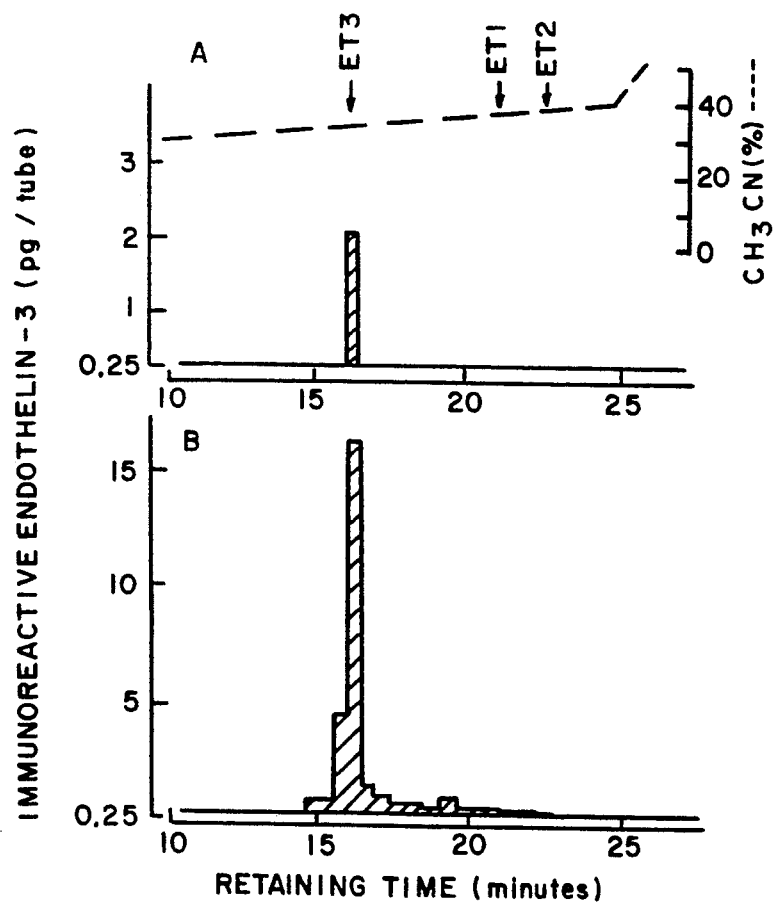

Detection of Immunological Activity of Endothelin-3 in Sera of Healthy Volunteers and Patients Undergoing Haemodialysis by RP-HPLC 20 ml of a serum of each healthy volunteer or 80 ml of a serum of each patient undergoing haemodialysis was diluted with the same amount of PBS, and passed through an AET-30a-bound Sepharose 4B column (containing 1.5 ml of a gel in which 1.5 mg of the antibody was bound to 1 g of CNBr-activated Sepharose 4B) at a rate of 10 ml/hr. The column was washed with 15 ml of PBS, and then eluted with 3 ml of a 60% acetonitrile solution containing 0.05% TFA, followed by concentration in a stream of nitrogen. The concentrate was dissolved in a 5% acetonitrile solution containing 0.05% TFA and 0.05% 3-[(3-cholamidopropyl)dimethylammonio]-1-propane- sulfonate (CHAPS), and then assayed by RP-HPLC under the conditions of elution described in Example 9. The results are shown in FIG. 8. From the fact that the immunological activity for both the healthy volunteers (A) and the patients undergoing haemodialysis (B) was detected at the elution position of standard synthetic endothelin-3, it was confirmed that the sandwich method-EIA detected endothelin-3 in the sera and its excellent property was revealed.

EXAMPLE 12

Examination of Neutralization of Monoclonal Antibody AET-30a

A spiral strip about 2 cm long delivered from the porcine left coronary artery was suspended in a Magnus tube filled with a Krebs-Henseleit solution (hereinafter referred to as a nutritive solution) while passing a mixed gas (95% $O_2$+5% $CO_2$) therethrough. After standing at 37° C. for 3 hours, the tension produced by the construction of the vascular smooth muscle was measured with an isometric transducer (Polygraph, NEC Saneisha). When the solution (with a final endothelin-3 concentration of $1 \times 10^{-8}$ M) of endothelin-3 previously reacted with 20-fold mole AET-30a at 37° C. for 20 minutes was added to the nutritive solution, the tension produced in the muscle was only 7.0% (n=5) of the tension produced therein by endothelin-3 having the same concentration. In contrast, when the solution (with a final concentration of $1 \times 10^{-8}$ M) of endothelin-3 previously reacted with control antibody H272-11 (carcinostatic fetal antigen) was added to the nutritive solution, the tension due to the constriction (121%, n=5) approximately equivalent to that produced by endothelin-3 was observed. The above finding proved that AET-30a neutralized the vascular smooth muscle constrictor activity of endothelin-3.

The monoclonal antibodies to endothelin-3 of the present invention have a very high affinity and can neutralize the vascular smooth muscle constrictor activity of endothelin-3. These monoclonal antibodies are used together with antibodies recognizing the C-terminal portion of endothelin-3 in sandwich immunoassays, whereby endothelin-3 can be determined with high sensitivity and without the cross reaction with endothelin-1, endothelin-2 or big endothelin-3.

Further, these antibodies can be used as strong antagonists to endothelin-3 in various diseases relating to endothelin-3.

Furthermore, the monoclonal antibodies to the big endothelin-3 C-terminal peptide of the present invention have wide specificity for the C-terminus of big endothelin-3. For this reason, these, antibodies are advantageously used together with monoclonal antibodies to endothelin-3 for detection of the immunological activity of big endothelin-3 in sandwich immunoassays, whereby big endothelin-3 can be determined with high sensitivity and without the cross reaction with endothelin-1, endothelin-2, endothelin-3 or big endothelin-1.

The following references, which are referred to for their disclosures at various points in this application, are incorporated herein by reference.

Japanese Patent Unexamined Publication No. 1-253797/1989

Japanese Patent Unexamined Publication No. 1-46560/1989

J. Am. Chem. Soc. 85, 2149 (1963)

The Peptides, vol. 1, Academic Press, New York, U.S.A. (1966)

Izumiya et al., Peptide Synthesis, Maruzen (1975)

Nature, 256, 495 (1975)

J. Appl. Biochem., 6, 56–63 (1984)

Current Topics in Microbiology and Immunology, 81, 1 (1978)

Clinic Chimica Acta, 331–340 (1987)

What is claimed is:

1. A monoclonal antibody which specifically binds to endothelin-3 and is obtained from AET-30, accession no. FERM BP-2523.

2. A monoclonal antibody which specifically binds to big endothelin-3 comprising an amino acid sequence substantially corresponding to Cys Thr Cys Phe Thr Tyr Lys Asp Lys Glu Cys
Val Tyr Tyr Cys His Leu Asp Ile Ile Trp Ile
Asn Thr Pro Glu Gln Thr Val Pro Tyr Gly Leu
Ser Asn Tyr Arg Gly Ser Phe Arg X, wherein X is Gly-OH or NH$_2$, or a portion thereof, said monoclonal antibody obtained from bET-31, accession no. FERM BP-2949, or from bET-23, accession no. FERM BP-2948.

3. A hybridoma which produces a monoclonal antibody which specifically binds to endothelin-3, said hybridoma obtained from AET-30, accession no. FERM BP-2523.

4. A hybridoma which produces a monoclonal antibody which specifically binds to big endothelin-3 comprising an amino acid sequence substantially corresponding to Cys Thr Cys Phe Thr Tyr Lys Asp Lys Glu Cys
Val Tyr Tyr Cys His Leu Asp Ile Ile Trp Ile
Asn Thr Pro Glu Gln Thr Val Pro Tyr Gly Leu
Ser Asn Tyr Arg Gly Ser Phe Arg X, wherein X is Gly-OH or NH$_2$, or a portion thereof, said hybridoma obtained from bET-31, accession no. FERM BP-2949, or from bET-23, accession no. FERM BP-2948.

5. A method for assaying endothelin-3 or big endothelin-3 in a test solution which comprises contacting the test solution with a monoclonal antibody insolubilized on a carrier, then contacting therewith a labeled monoclonal antibody, and measuring an activity of a labeling agent on the insolubilized carrier, wherein one of the monoclonal antibody insolubilized on a carrier and the labeled monoclonal antibody specifically binds to endothelin-3 and is obtained from AET-30, accession no. FERM BP-2523, and the other of the monoclonal antibody insolubilized on a carrier and the labeled monoclonal antibody specifically binds to bid endothelin-3 comprising an amino acid sequence substantially corresponding to Cys Thr Cys Phe Thr Tyr Lys Asp Lys Glu Cys
Val Tyr Tyr Cys His Leu Asp Ile Ile Trp Ile
Asn Thr Pro Glu Gln Thr Val Pro Tyr Gly Leu
Ser Asn Tyr Arg Gly Ser Phe Arg X, wherein X is Gly-OH or NH$_2$, or a portion thereof, and is obtained from bET-31, accession no. FERM BP-2949, or from bER-23, accession no. FERM BP-2948.

6. The method of claim 5 where the monoclonal antibody insolubilized on a carrier is obtained from AET-30, accession no. FERM BP-2523, and the labeled monoclonal antibody is obtained from bER-31, accession no. FERM BP-2949, or from bER-23, accession no. FERM BP-2948.

* * * * *